(12) United States Patent
Mao et al.

(10) Patent No.: US 12,702,502 B2
(45) Date of Patent: Aug. 11, 2026

(54) SYSTEMS AND METHODS FOR DYNAMIC ADJUSTMENTS BASED ON LOAD INPUTS FOR ROBOTIC SYSTEMS

(71) Applicant: Auris Health, Inc., Redwood City, CA (US)

(72) Inventors: Ying Mao, San Mateo, CA (US); Nicholas J. Eyre, Redwood City, CA (US); Mason Myles Markee, Pacifica, CA (US); Alexander Tarek Hassan, San Francisco, CA (US)

(73) Assignee: AURIS HEALTH, INC., Santa Clara, CA (US)

( * ) Notice: Subject to any disclaimer, the term of this patent is extended or adjusted under 35 U.S.C. 154(b) by 96 days.

(21) Appl. No.: 18/419,172

(22) Filed: Jan. 22, 2024

(65) Prior Publication Data

US 2024/0238054 A1 Jul. 18, 2024

Related U.S. Application Data

(63) Continuation of application No. 17/154,356, filed on Jan. 21, 2021, now Pat. No. 11,925,424.

(Continued)

(51) Int. Cl.

*A61B 34/30* (2016.01)
*A61B 90/00* (2016.01)

(Continued)

(52) U.S. Cl.

CPC .............. *A61B 34/30* (2016.02); *A61B 90/06* (2016.02); *A61B 90/50* (2016.02); *G16H 20/40* (2018.01);

(Continued)

(58) Field of Classification Search

CPC ......... A61B 34/30; A61B 90/06; A61B 90/50; A61B 2034/301; A61B 2034/302;

(Continued)

(56) References Cited

U.S. PATENT DOCUMENTS

| | | | |
|---|---|---|---|
| 7,837,674 | B2 | 11/2010 | Cooper |
| 8,786,241 | B2 | 7/2014 | Nowlin et al. |

(Continued)

FOREIGN PATENT DOCUMENTS

| | | | |
|---|---|---|---|
| EP | 1815949 | A1 | 8/2007 |
| EP | 2783800 | A2 | 2/2014 |

(Continued)

OTHER PUBLICATIONS

Notice of Allowance dated Oct. 20, 2023; U.S. Appl. No. 17/154,356, filed Jan. 21, 2021; 13 pages.

(Continued)

*Primary Examiner* — Kira Nguyen

(74) *Attorney, Agent, or Firm* — FBT Gibbons LLP

(57) ABSTRACT

Systems and methods for dynamic adjustments based on load inputs for robotic systems are provided. In one aspect, a robotic system includes a first robotic arm having at least one joint, a set of one or more processors, and at least one computer-readable memory in communication with the set of one or more processors and having stored thereon computer-executable instructions. The computer executable instructions cause the one or more processors to determine a first external load threshold for the at least one joint based on a maximum safe load capability of the first robotic arm, and adjust the first external load threshold during a medical procedure.

20 Claims, 25 Drawing Sheets

Related U.S. Application Data

(60) Provisional application No. 62/992,010, filed on Mar. 19, 2020.

(51) Int. Cl.
*A61B 90/50* (2016.01)
*G16H 20/40* (2018.01)
*G16H 40/63* (2018.01)

(52) U.S. Cl.
CPC ........ *G16H 40/63* (2018.01); *A61B 2034/301* (2016.02); *A61B 2034/302* (2016.02); *A61B 2034/303* (2016.02); *A61B 2090/066* (2016.02); *A61B 2562/0219* (2013.01); *A61B 2562/0252* (2013.01)

(58) Field of Classification Search
CPC ........ A61B 2034/303; A61B 2090/066; A61B 2562/0219; A61B 2562/0252; A61B 2034/2055; A61B 34/20; A61B 34/25; A61B 2017/00154; A61B 2034/2051; A61B 2090/064; A61B 2090/0811; G16H 20/40; G16H 40/63; B25J 9/1689; B25J 13/085; G05B 2219/33019
USPC .......................................................... 700/245
See application file for complete search history.

(56) References Cited

U.S. PATENT DOCUMENTS

| | | | | |
|---|---|---|---|---|
| 9,763,741 | B2 | 9/2017 | Alvarez et al. | |
| 10,145,747 | B1 * | 12/2018 | Lin | A61B 90/06 |
| 10,194,998 | B2 | 2/2019 | Nowlin et al. | |
| 10,617,480 | B2 | 4/2020 | Brisson | |
| 11,160,625 | B2 | 11/2021 | Wixey et al. | |
| 11,925,424 | B2 | 3/2024 | Mao et al. | |
| 2017/0156808 | A1 * | 6/2017 | Auld | A61B 34/70 |
| 2017/0265948 | A1 | 9/2017 | Prisco et al. | |
| 2018/0296299 | A1 | 10/2018 | Iceman | |
| 2019/0201145 | A1 * | 7/2019 | Shelton, IV | A61B 17/320068 |
| 2020/0268461 | A1 * | 8/2020 | Forstein | A61B 34/32 |
| 2020/0360100 | A1 * | 11/2020 | Mantri | A61B 90/37 |
| 2021/0077204 | A1 * | 3/2021 | Zubiate | A61B 34/30 |
| 2021/0290320 | A1 | 9/2021 | Mao et al. | |
| 2021/0298850 | A1 | 9/2021 | Huang et al. | |
| 2022/0219320 | A1 * | 7/2022 | Søe-Knudsen | B25J 9/1633 |

FOREIGN PATENT DOCUMENTS

| | | | |
|---|---|---|---|
| JP | 2004025387 | A | 1/2004 |
| JP | 2007066001 | A | 3/2007 |
| KR | 20180041218 | A | 4/2018 |
| WO | 2017095768 | A1 | 6/2017 |
| WO | 2017209695 | A1 | 12/2017 |
| WO | 2019136039 | A1 | 7/2019 |

OTHER PUBLICATIONS

PCT International Search Report; Application No. PCT/IB2021/050466; Apr. 19, 2021; 9 pages.

PCT Written Opinion of the International Searching Authority; Application No. PCT/IB2021/050466; Apr. 19, 2021; 3 pages.

European Extended Search Report; Application No. 21771242.1; Mar. 27, 2024; 8 pages.

Chinese First Office Action and Search Report dated Jul. 24, 2025, for Application No. 202180022250.3, 15 pages.

European Communication dated Nov. 10, 2025, for Application No. 21771242.1, 4 pages.

* cited by examiner

63

SYSTEMS AND METHODS FOR DYNAMIC ADJUSTMENTS BASED ON LOAD INPUTS FOR ROBOTIC SYSTEMS

CROSS-REFERENCE TO RELATED APPLICATIONS

This application is a continuation of U.S. patent application Ser. No. 17/154,356 filed Jan. 21, 2021 by Ying Mao, et al., issued as U.S. Pat. No. 11,925,424 on Mar. 12, 2024, entitled, "Systems and Methods for Dynamic Adjustments Based on Load Inputs for Robotic Systems", which claims priority to U.S. Provisional Application No. 62/992,010 filed Mar. 19, 2020, both of which are incorporated by reference herein in their entireties.

TECHNOLOGICAL FIELD

The systems and methods disclosed herein are directed to systems and methods for adjusting robotic arm parameters, and more particularly to adjusting external load thresholds and remote centers of motion.

BACKGROUND

Medical procedures, such as laparoscopy, may involve accessing an internal region of a patient using one or more robotic arms to insert medical instrument(s) into the internal region of the patient. In a laparoscopic procedure, the medical instrument(s) can be inserted into the internal region of a patient through a cannula.

In certain procedures, a robotically-enabled medical system may be used to control the insertion and/or manipulation of one or more medical instrument(s). In order to avoid injuring a patient, it can be important for the medical system to reduce the risk of the medical instrument(s) exerting excessive forces onto the patient.

SUMMARY

The systems, methods and devices of this disclosure each have several innovative aspects, no single one of which is solely responsible for the desirable attributes disclosed herein.

In one aspect, there is provided a robotic system, comprising: a first robotic arm having at least one joint; a set of one or more processors; and at least one computer-readable memory in communication with the set of one or more processors and having stored thereon computer-executable instructions to cause the one or more processors to: determine a first external load threshold for the at least one joint based on a maximum safe load capability of the first robotic arm, and adjust the first external load threshold during a medical procedure.

In certain implementations, the computer-executable instructions further cause the one or more processors to: determine a load applied to the at least one joint due to at least one of gravity and inertia of the first robotic arm.

In certain implementations, the first external load threshold is further determined based on the maximum safe load capability minus the at least one of the gravity load and the inertial load.

In certain implementations, the first external load threshold is adjusted in response to changes in pose of the first robotic arm.

In certain implementations, the robotic system further comprises a second robotic arm, wherein: the computer-executable instructions further cause the one or more processors to determine a second external load threshold for the second robotic arm, and the first external load threshold is different from the second external load threshold.

In certain implementations, the maximum safe load capability is fixed.

In certain implementations, the maximum safe load capability varies based on time or temperature.

In certain implementations, the first robotic arm includes one or more sensors configured to detect an external load.

In certain implementations, the one or more sensors comprise one or more torque sensors.

In certain implementations, the one or more sensors comprise an end effector load cell.

In certain implementations, the computer-executable instructions further cause the one or more processors to: determine that the external load for the at least one joint exceeds the first external load threshold based on signals received from the one or more sensors, and restrict or prevent further movement of the first robotic arm in response to determining that the external load for the at least one joint exceeds the first external load threshold.

In certain implementations, the first robotic arm comprises one or more brakes configured to maintain a pose of the first robotic arm, the one or more brakes have a set holding torque, and the first external load threshold is further determined based on the holding torque of the one or more brakes.

In certain implementations, the one or more brakes are further configured to maintain the pose of the first robotic arm when the robotic arm is powered off or the robotic arm is in a fault state.

In another aspect, there is provided robotic system, comprising: a first robotic arm having a series of joints; one or more processors; and at least one computer-readable memory in communication with the one or more processors and having stored thereon a maximum safe load capability for each of the joints of the first robotic arm and computer-executable instructions to cause the one or more processors to: determine a load applied to each of the joints due to at least one of gravity or inertia of the first robotic arm, and set a first maximum external load threshold for each of the joints based on the maximum safe load capability of the corresponding joint and the at least one of the gravity load and the inertial load.

In certain implementations, the computer-executable instructions further cause the one or more processors to: adjust the first maximum external load threshold for one or more of the joints during a medical procedure.

In certain implementations, the first maximum external load threshold is adjusted in response to changes in poses of the first robotic arm.

In certain implementations, the robotic system further comprises a second robotic arm, wherein: the computer-executable instructions further cause the one or more processors to determine a second maximum external load threshold for the second robotic arm, and the first maximum external load threshold is different from the second maximum external load threshold.

In certain implementations, the maximum safe load capability for at least one of the joints is fixed.

In certain implementations, the maximum safe load capability varies based on time or temperature.

In certain implementations, the first robotic arm includes one or more sensors configured to detect an external load.

In certain implementations, the one or more sensors comprise one or more torque sensors.

In certain implementations, the one or more sensors comprise an end effector load cell.

In certain implementations, the computer-executable instructions further cause the one or more processors to: determine that the external load for at least one of the joints exceeds the corresponding first maximum load external threshold based signals received from the one or more sensors, and restrict or prevent further movement of the first robotic arm in response to determining that the external load for the at least one joint exceeds the first maximum external load threshold.

In certain implementations, the first robotic arm includes a series of brakes respectively positioned at the joints and configured to maintain a pose of the robotic arm, the brakes have a set holding torque and the first maximum external load threshold is further determined based on the maximum acceptable force of the brakes.

In certain implementations, the series of brakes are further configured to maintain the pose of the robotic arm when the robotic arm is powered off or the robotic arm is in a fault state.

In certain implementations, the computer-executable instructions further cause the one or more processors to: determine a maximum safe load capability of the first robotic arm based on a combination of first maximum external load thresholds for the joints.

In yet another aspect, there is provided a robotic system, comprising: a robotic arm configured to be coupled to a cannula; a set of one or more processors; and at least one computer-readable memory in communication with the set of one or more processors and having stored thereon computer-executable instructions to cause the set of one or more processors to: control the robotic arm to pivot the cannula about a remote center of motion; and adjust a position of the remote center of motion.

In certain implementations, the computer-executable instructions further cause the set of one or more processors to: measure a force exerted on a cannula by a body wall of a patient, and adjust the position of the remote center of motion based on the measured force between the cannula and the body wall of the patient.

In certain implementations, the computer-executable instructions further cause the one or more processors to: adjust the position of the remote center of motion within a predetermined area.

In certain implementations, the predetermined area is spherical.

In certain implementations, the computer-executable instructions further cause the one or more processors to: adjust the position of the remote center of motion based on a kinematic constraint.

In certain implementations, the kinematic constraint is a collision.

In certain implementations, the computer-executable instructions further cause the one or more processors to: adjust the position of the remote center of motion intraoperatively.

In certain implementations, the computer-executable instructions further cause the one or more processors to: adjust the position of the remote center of motion to provide an additional degree-of-freedom for collision avoidance.

In certain implementations, the computer-executable instructions further cause the one or more processors to: adjust the position of the remote center of motion to increase a reach of the robotic arm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
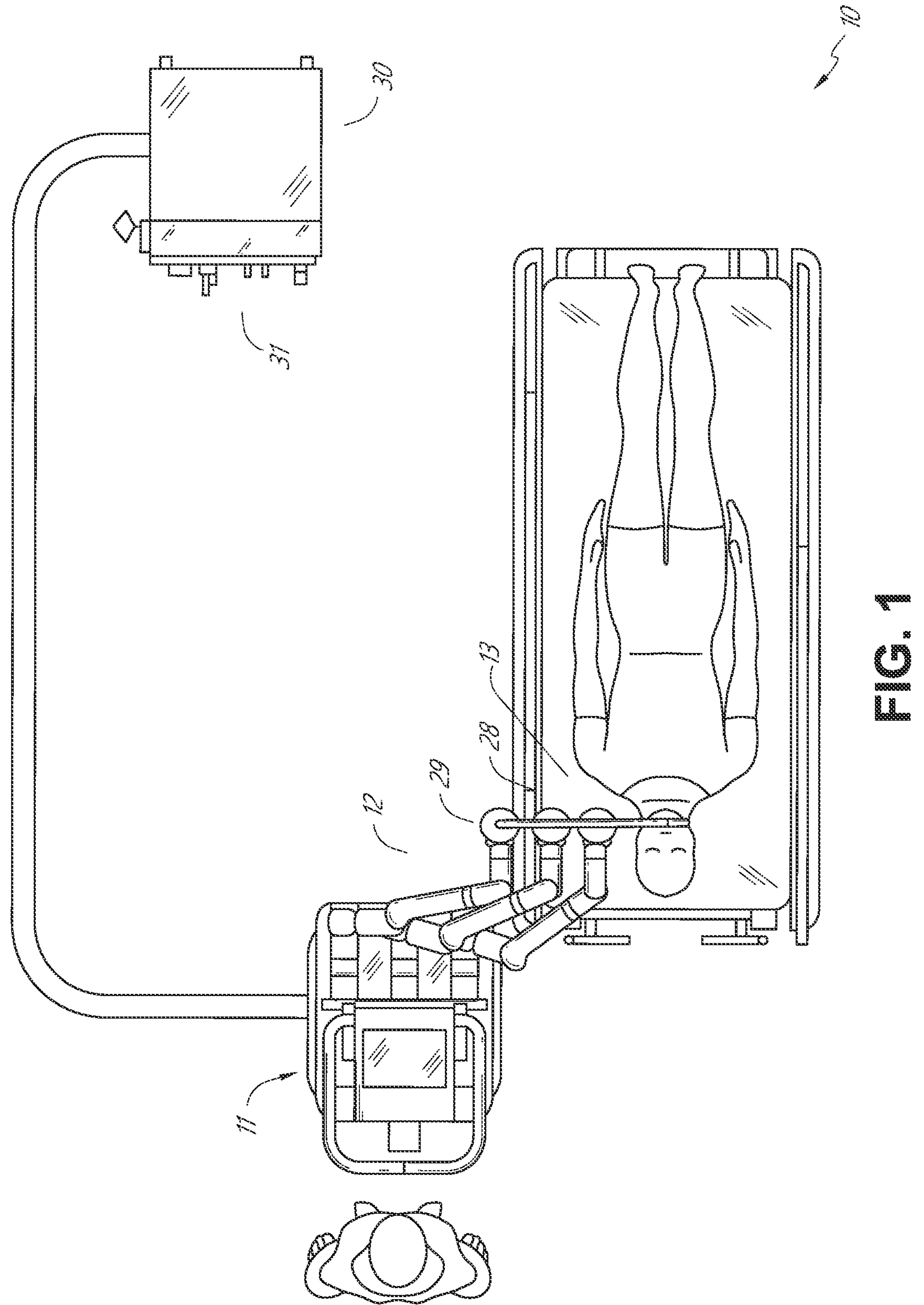
FIG. 1 illustrates an embodiment of a cart-based robotic system arranged for diagnostic and/or therapeutic bronchoscopy.
Figure 2:
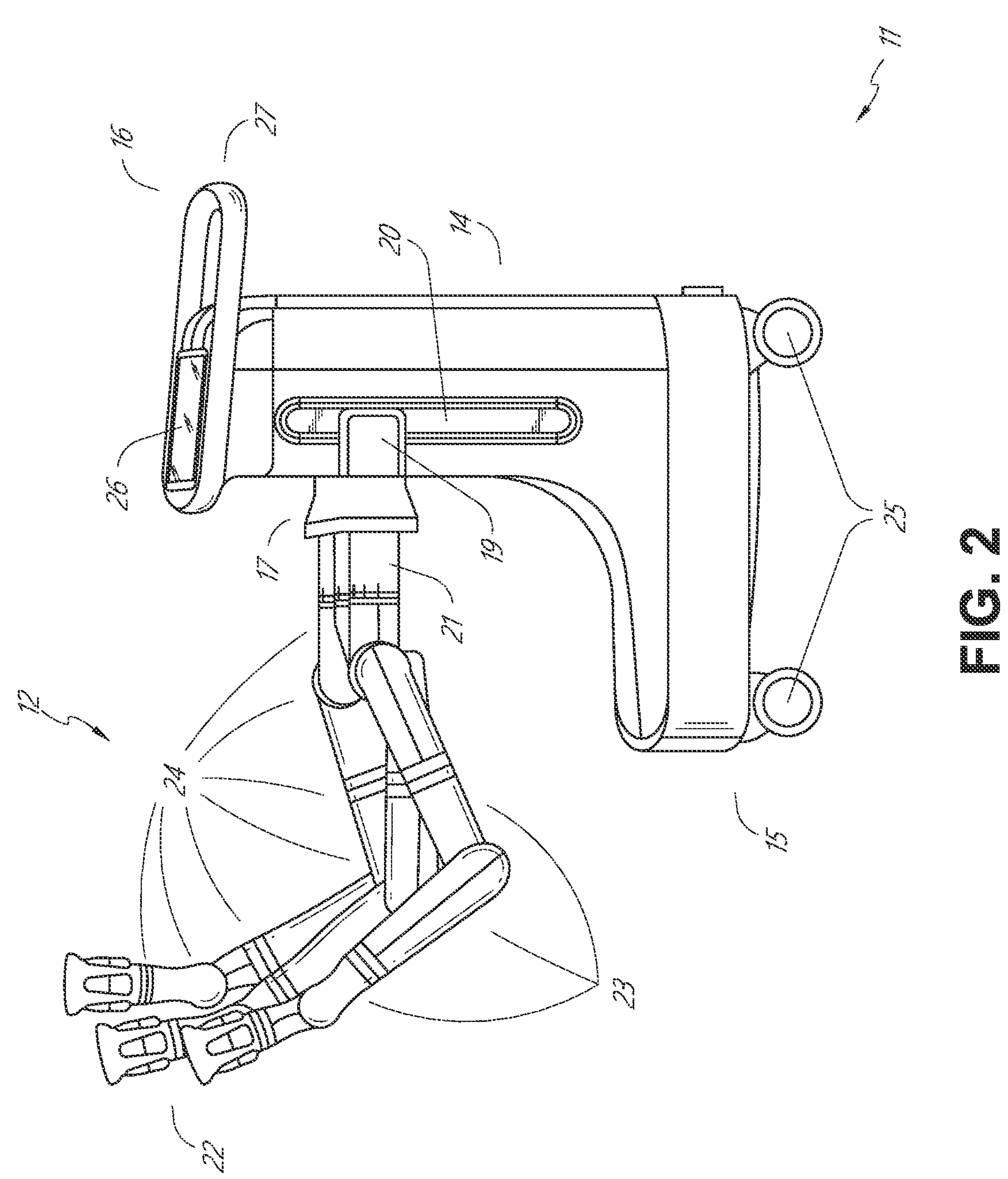
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to facilitate proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
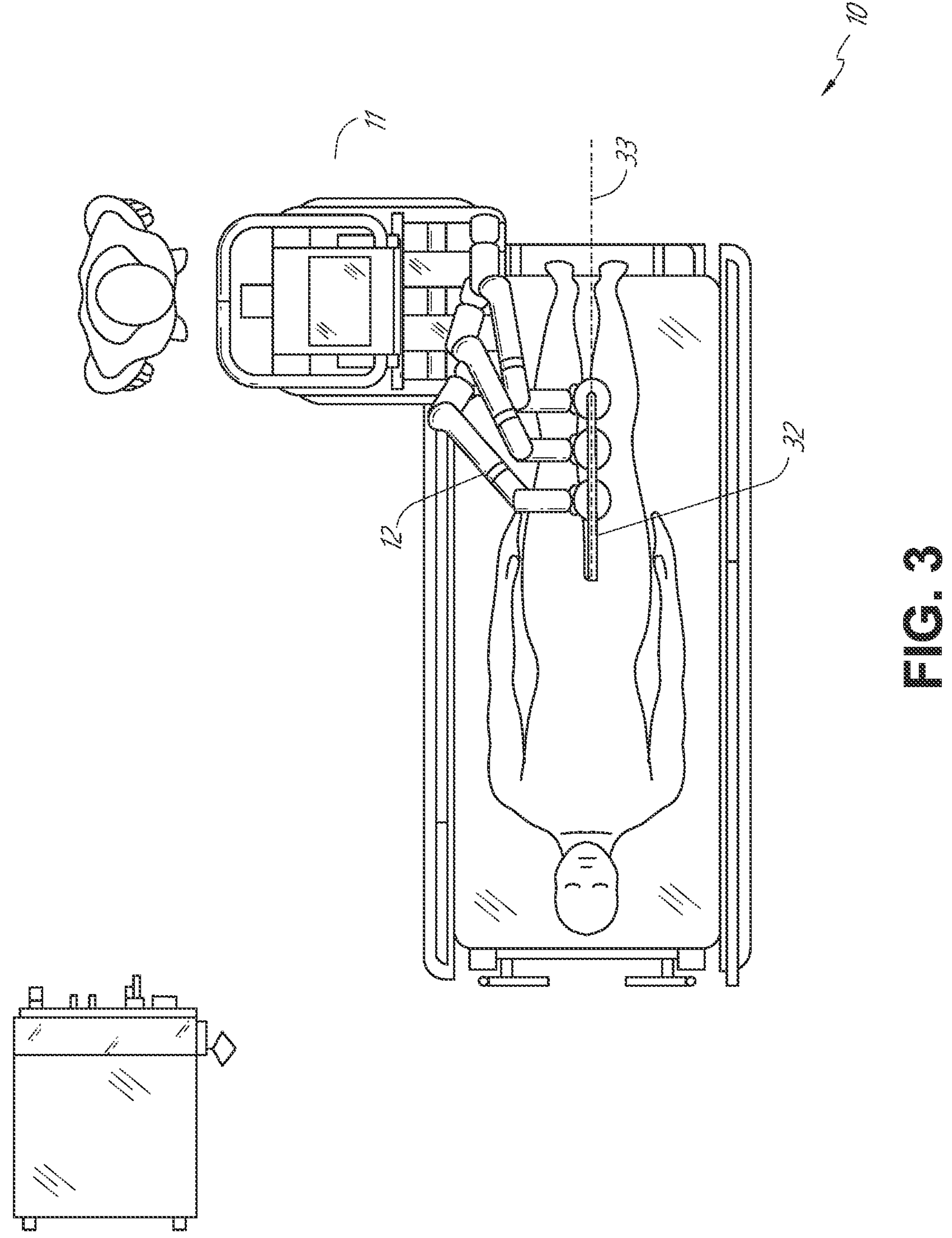
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
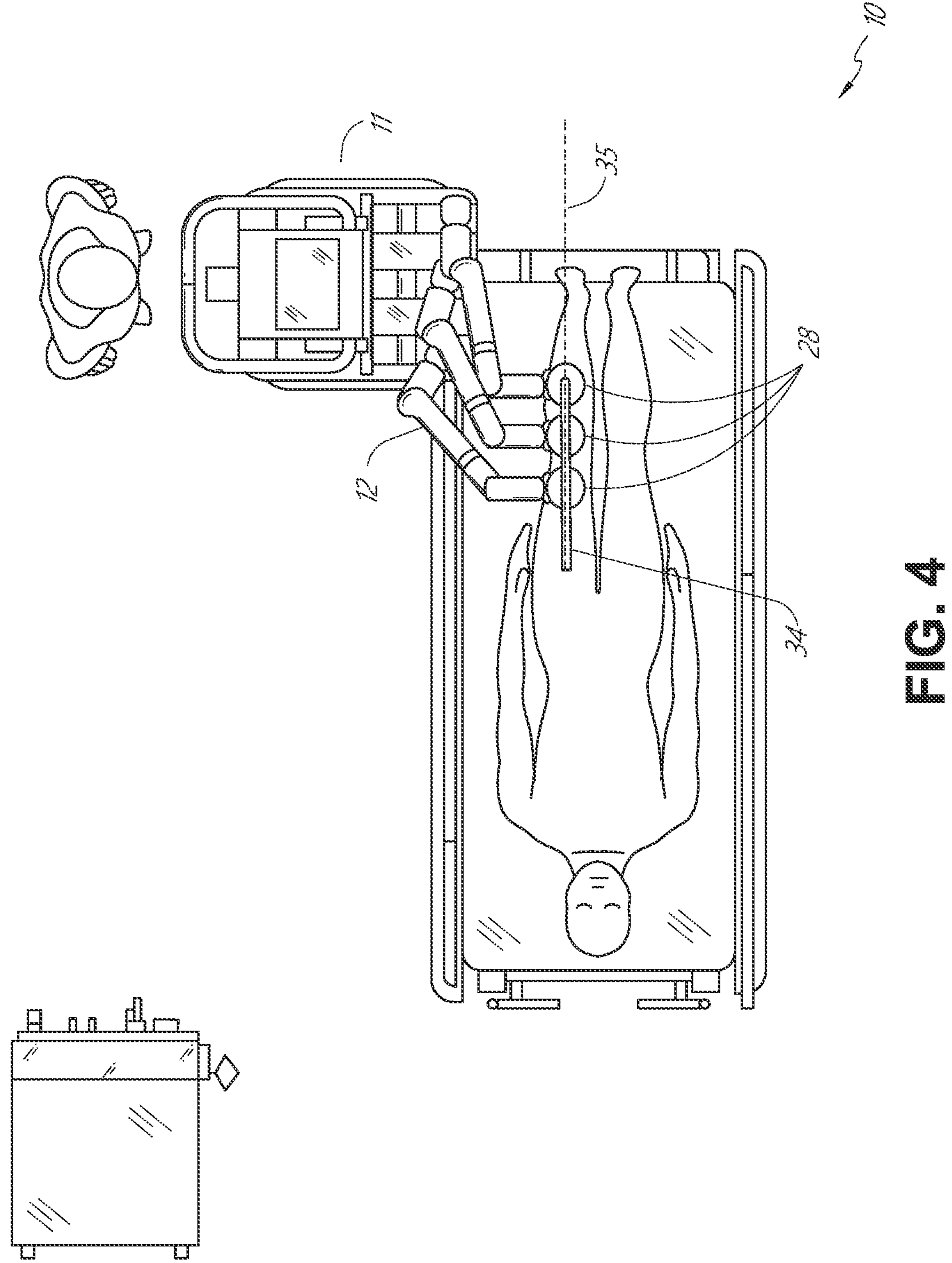
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
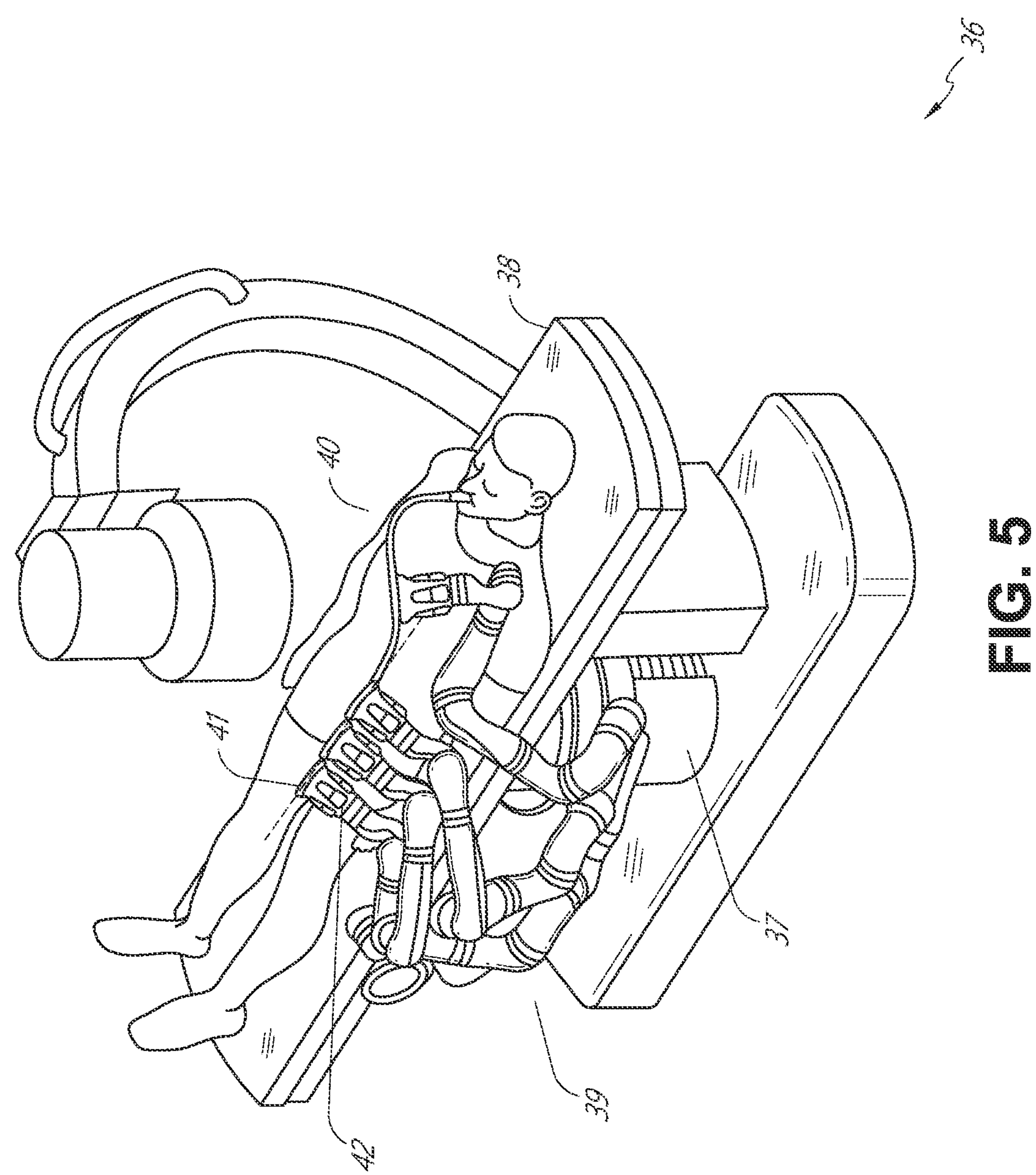
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
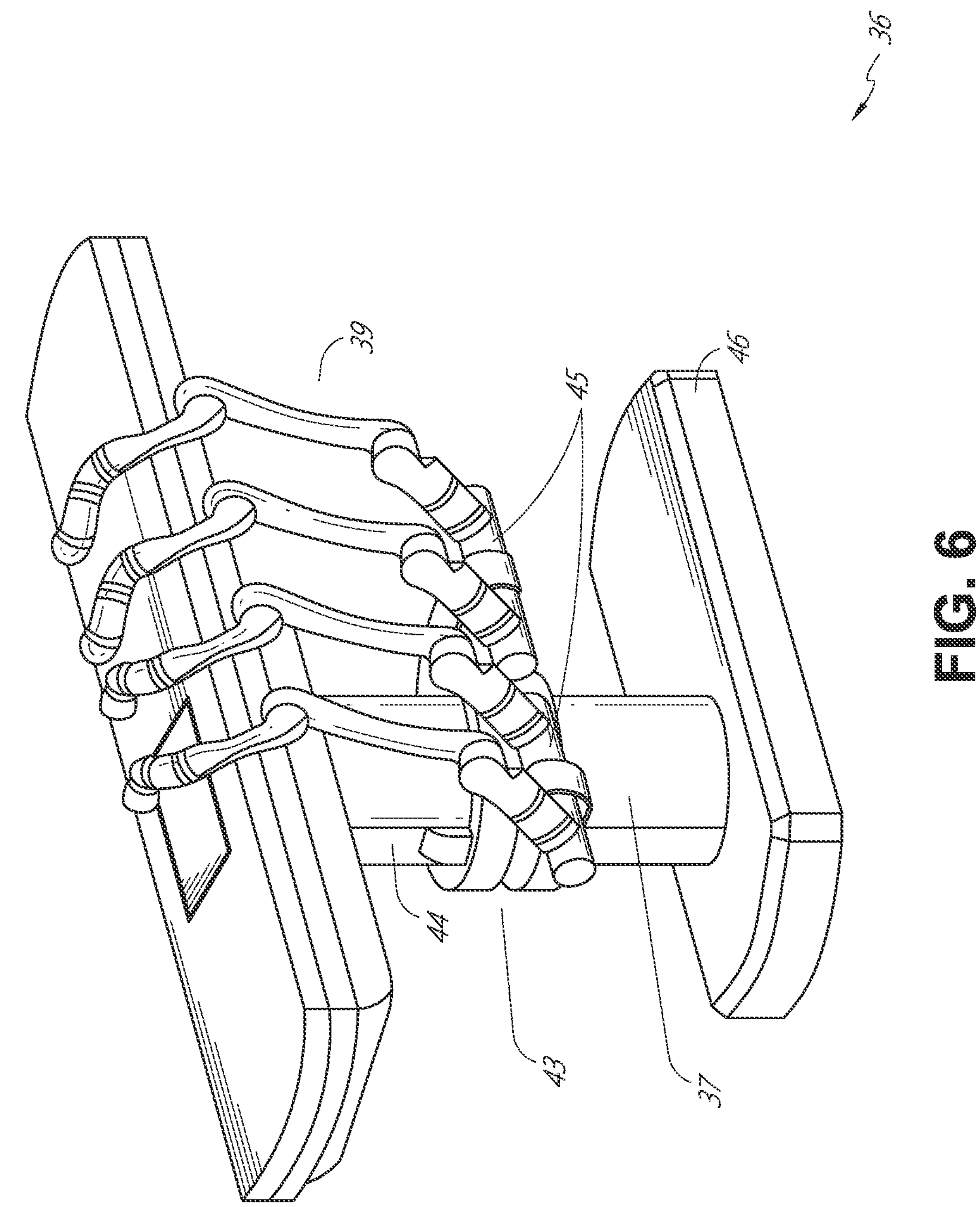
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
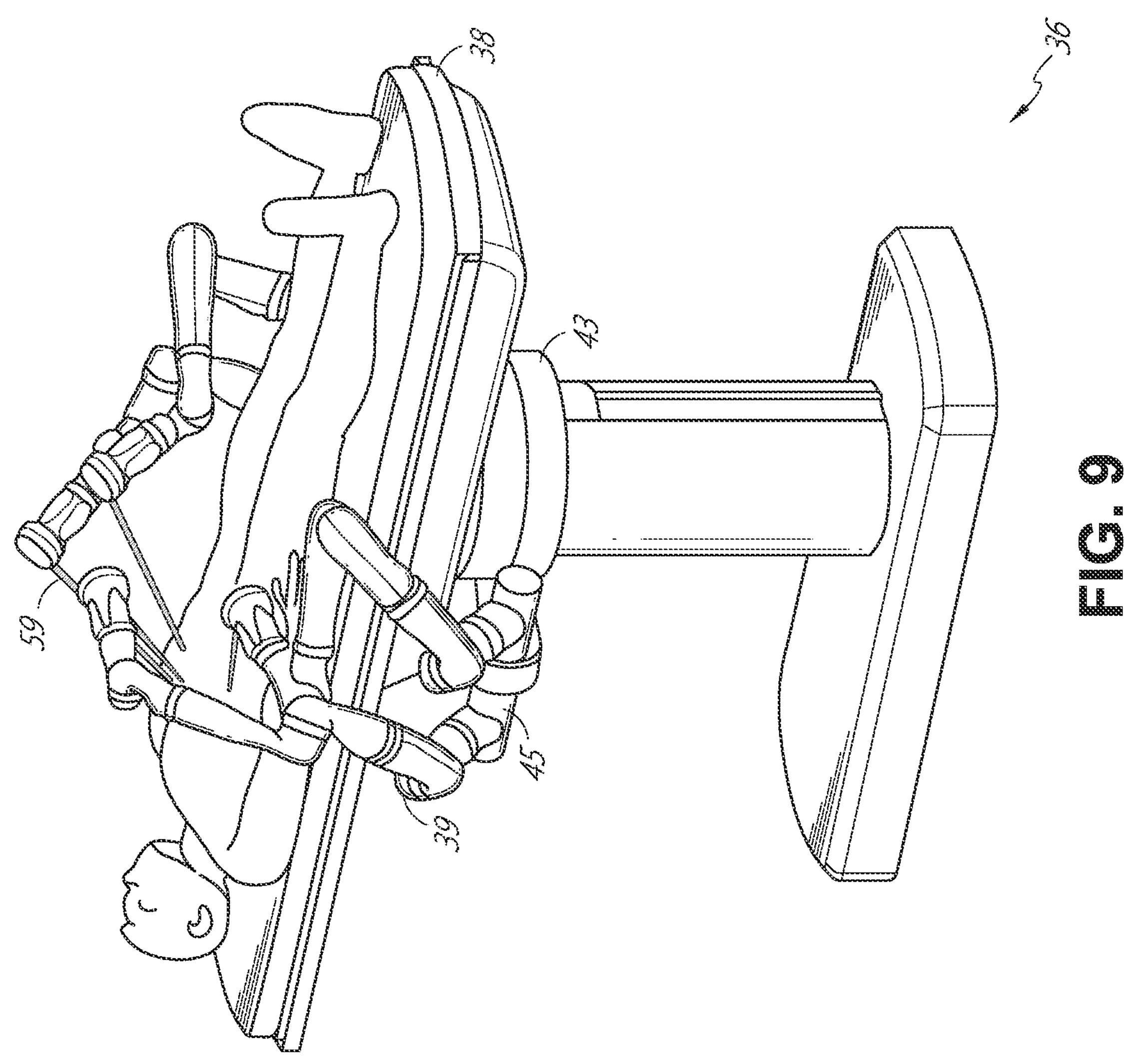
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
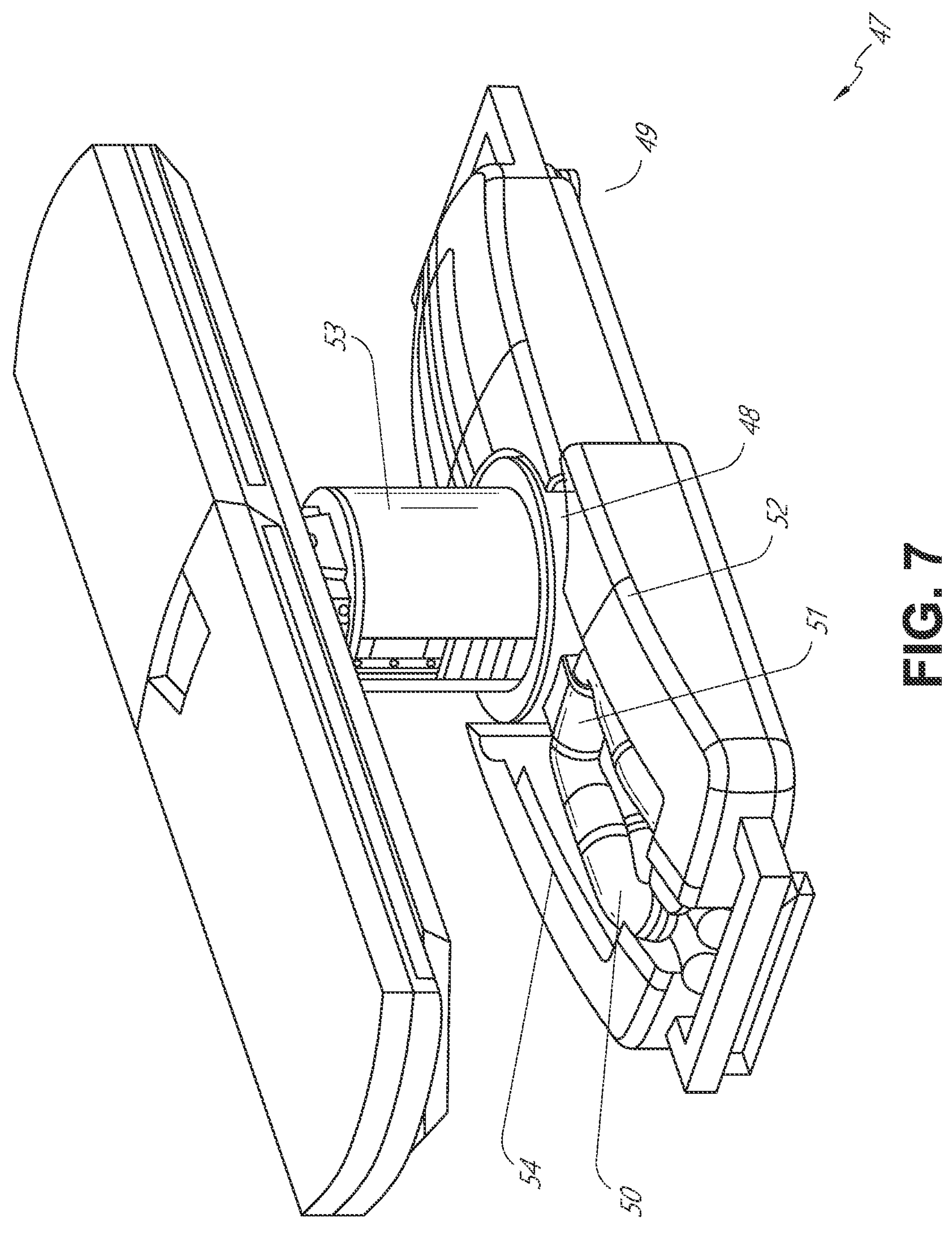
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
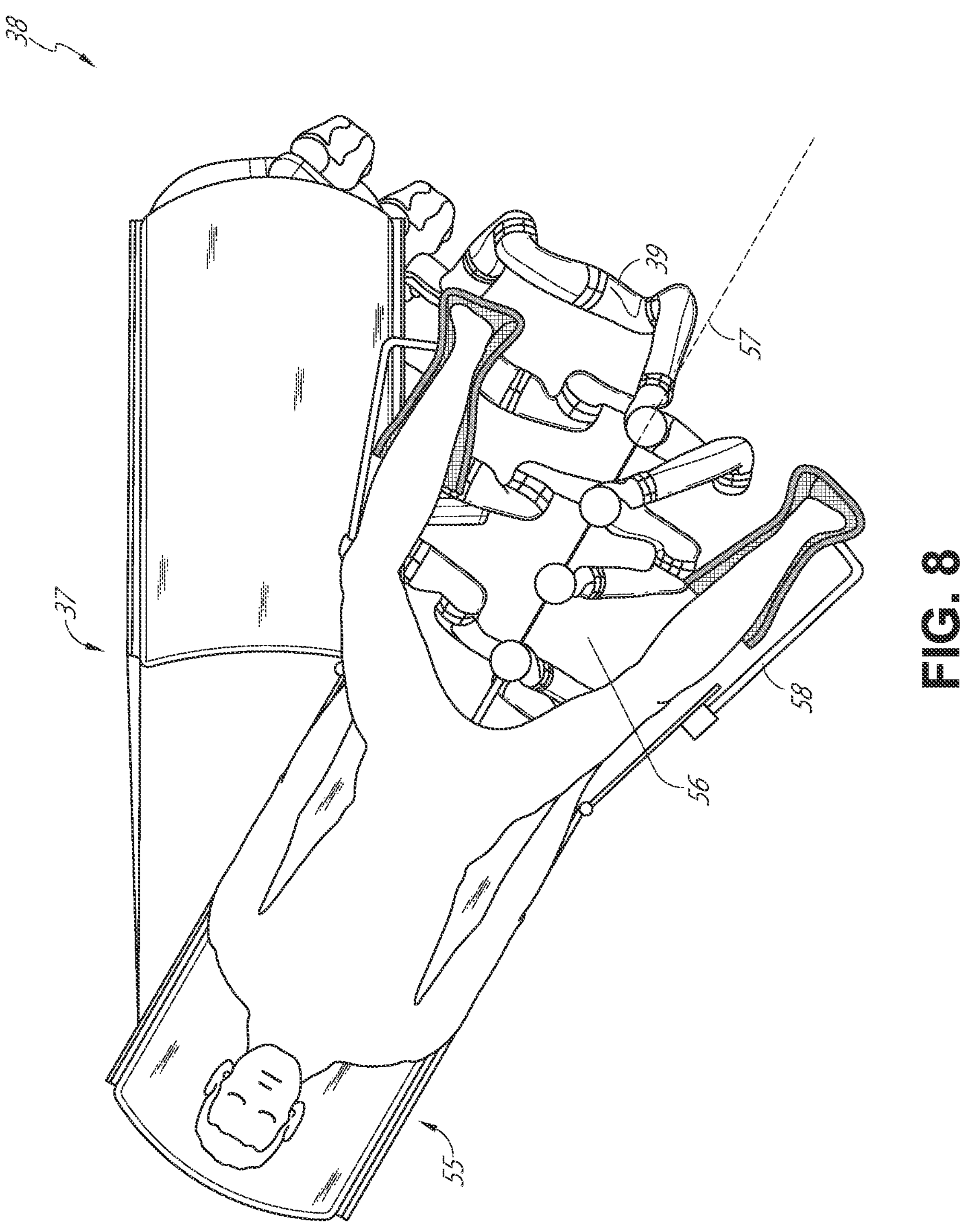
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope.

FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
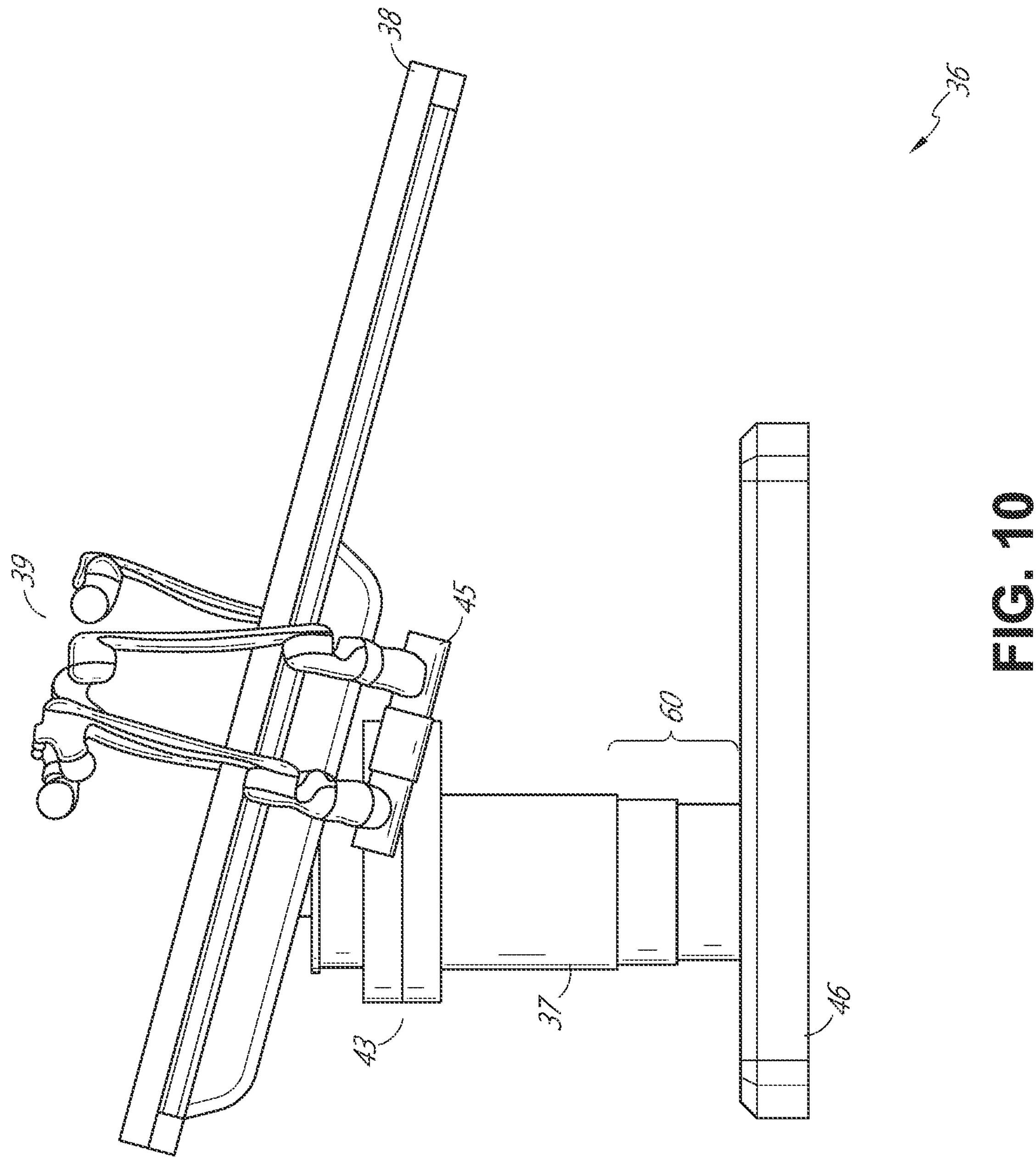
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
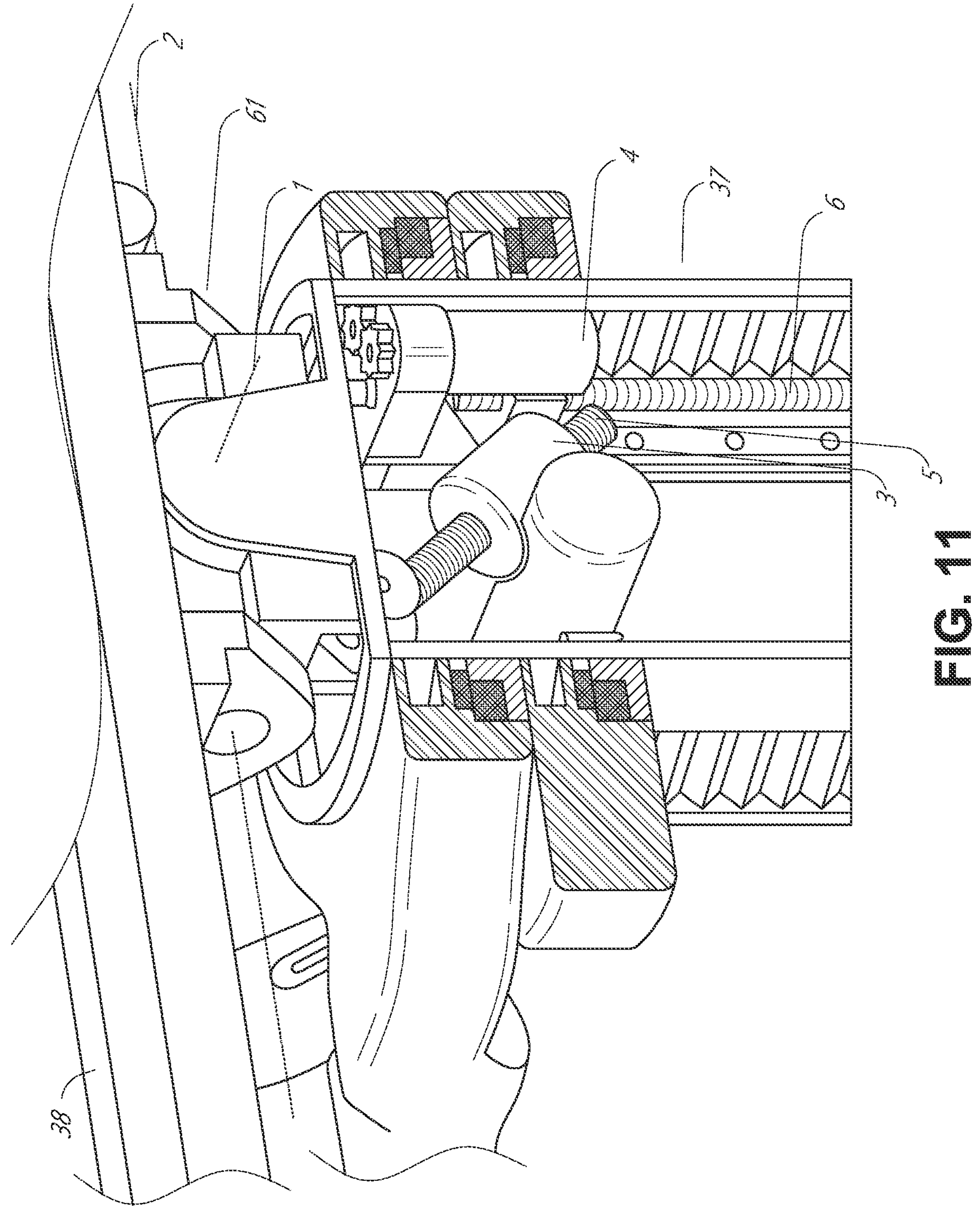
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figures 12, 13:
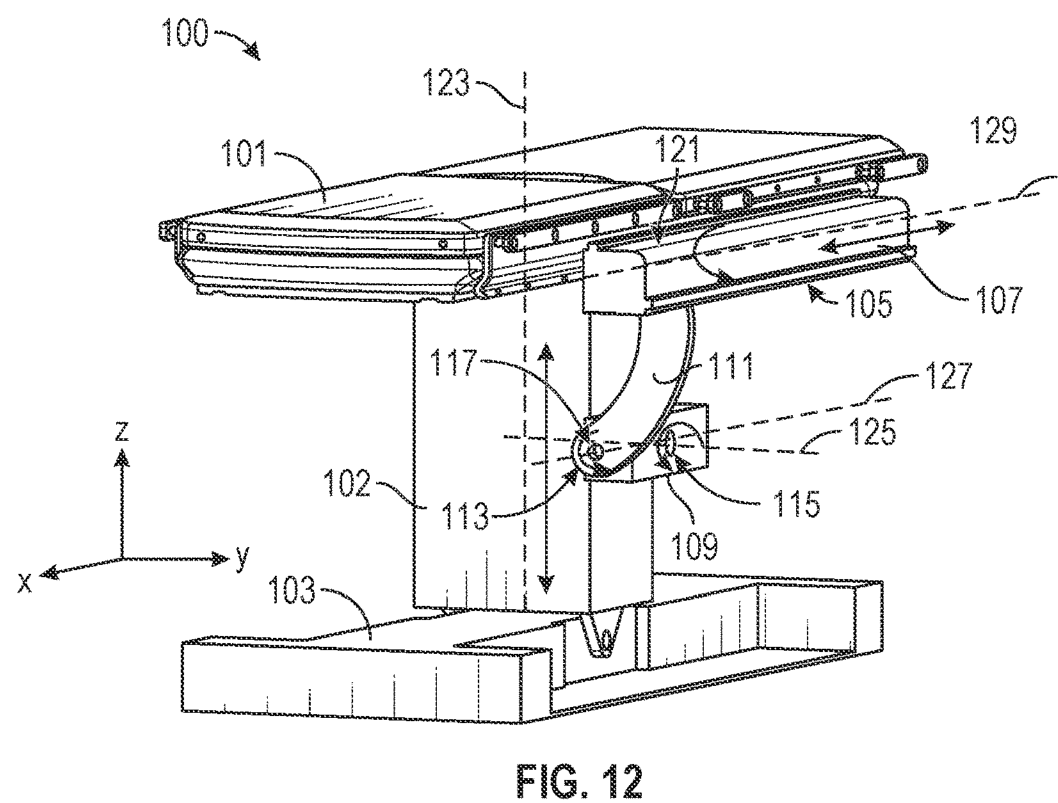
FIG. 12 illustrates an alternative embodiment of a table-based robotic system.
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
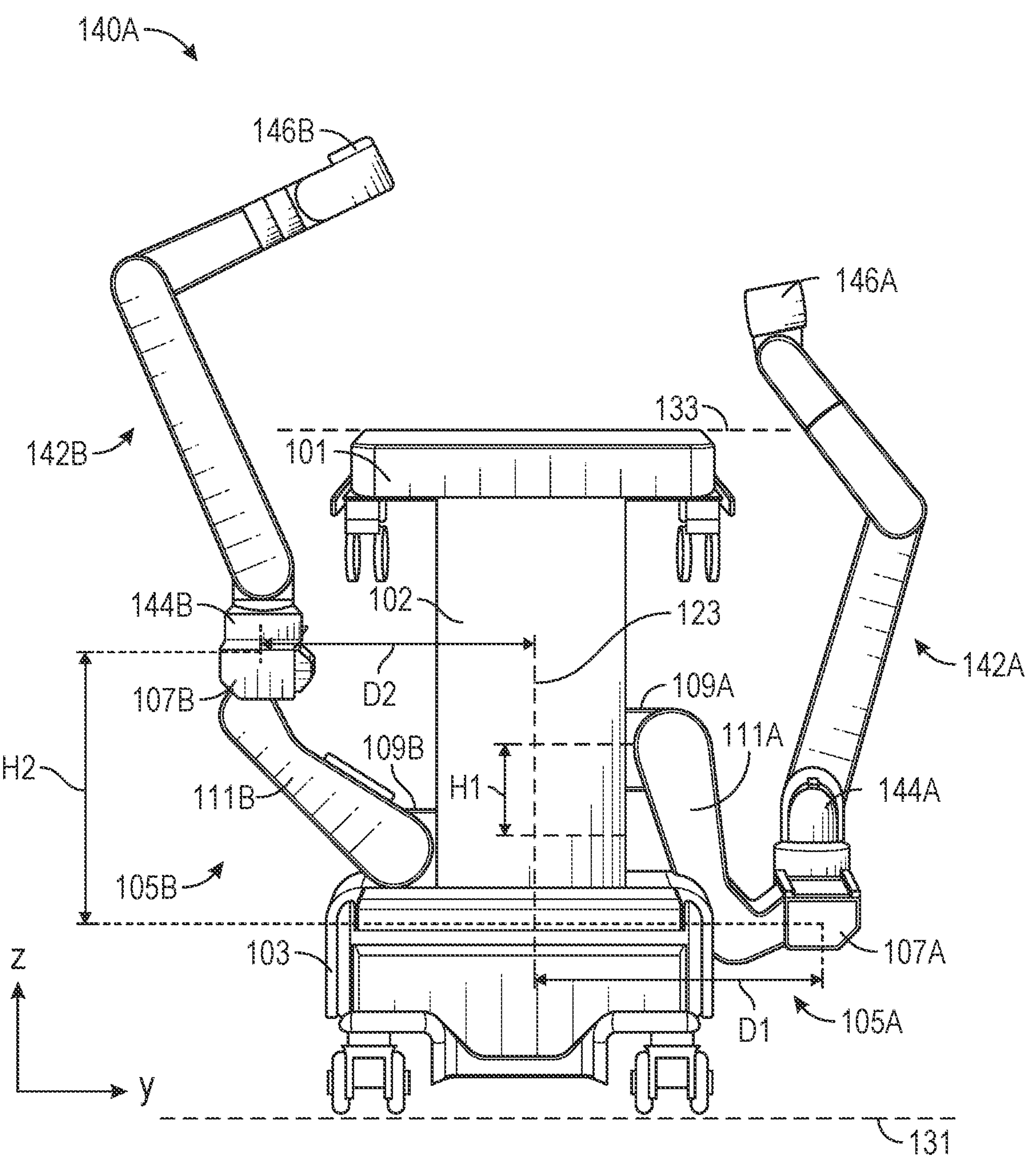
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
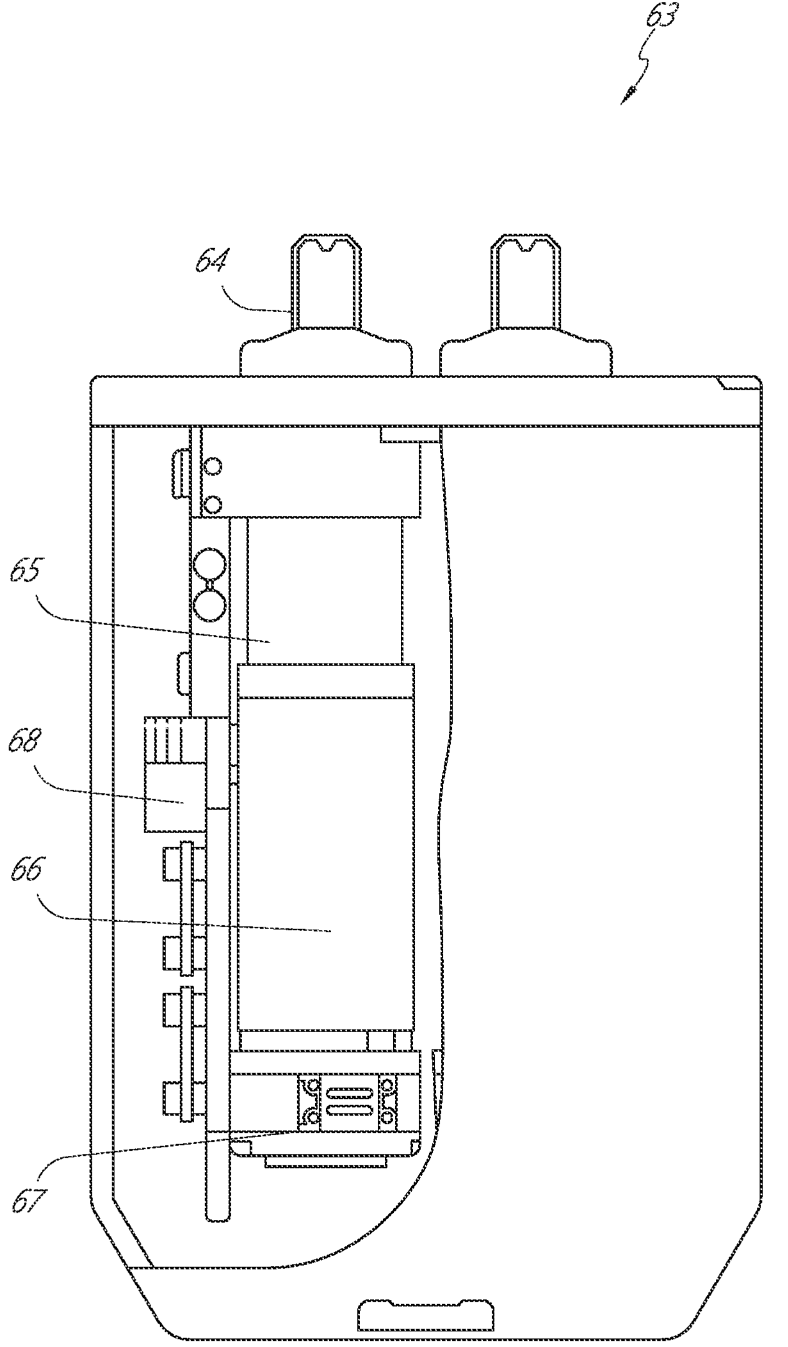
FIG. 15 illustrates an exemplary instrument driver.
Figure 15:

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
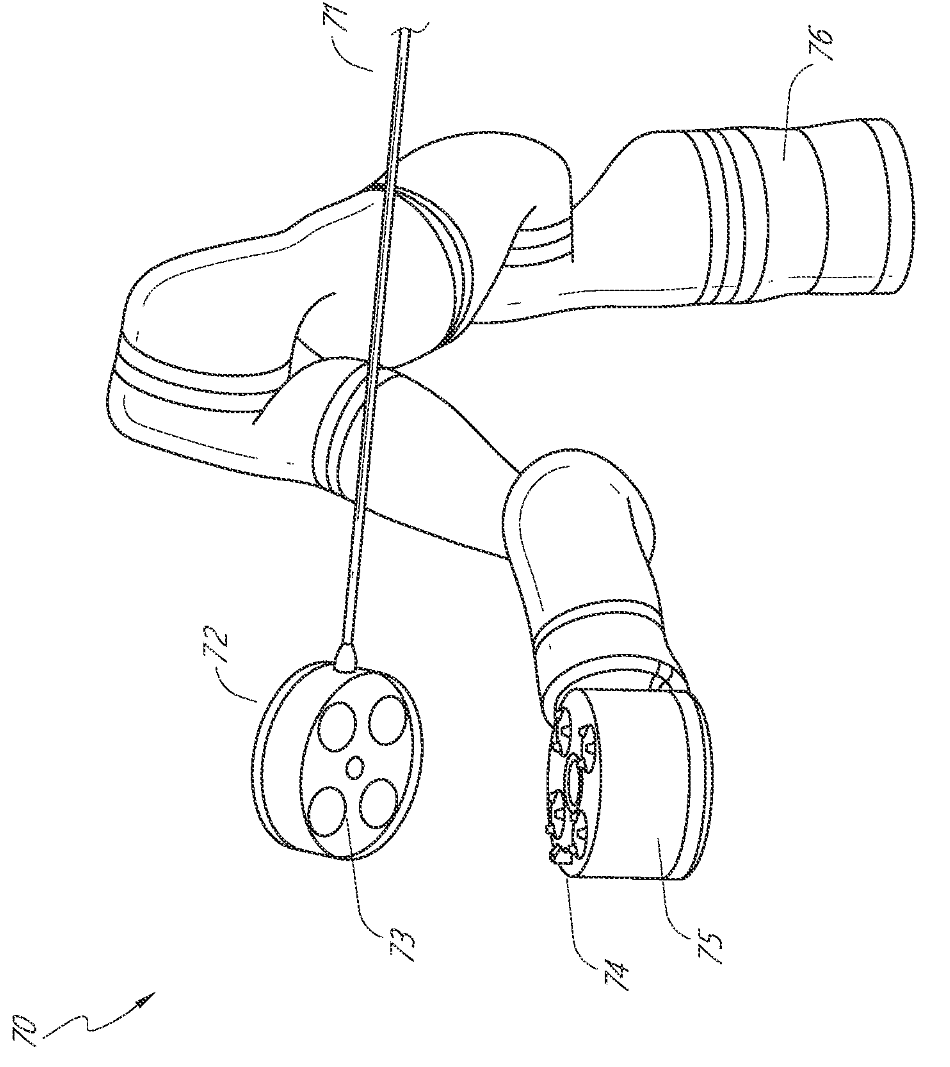
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
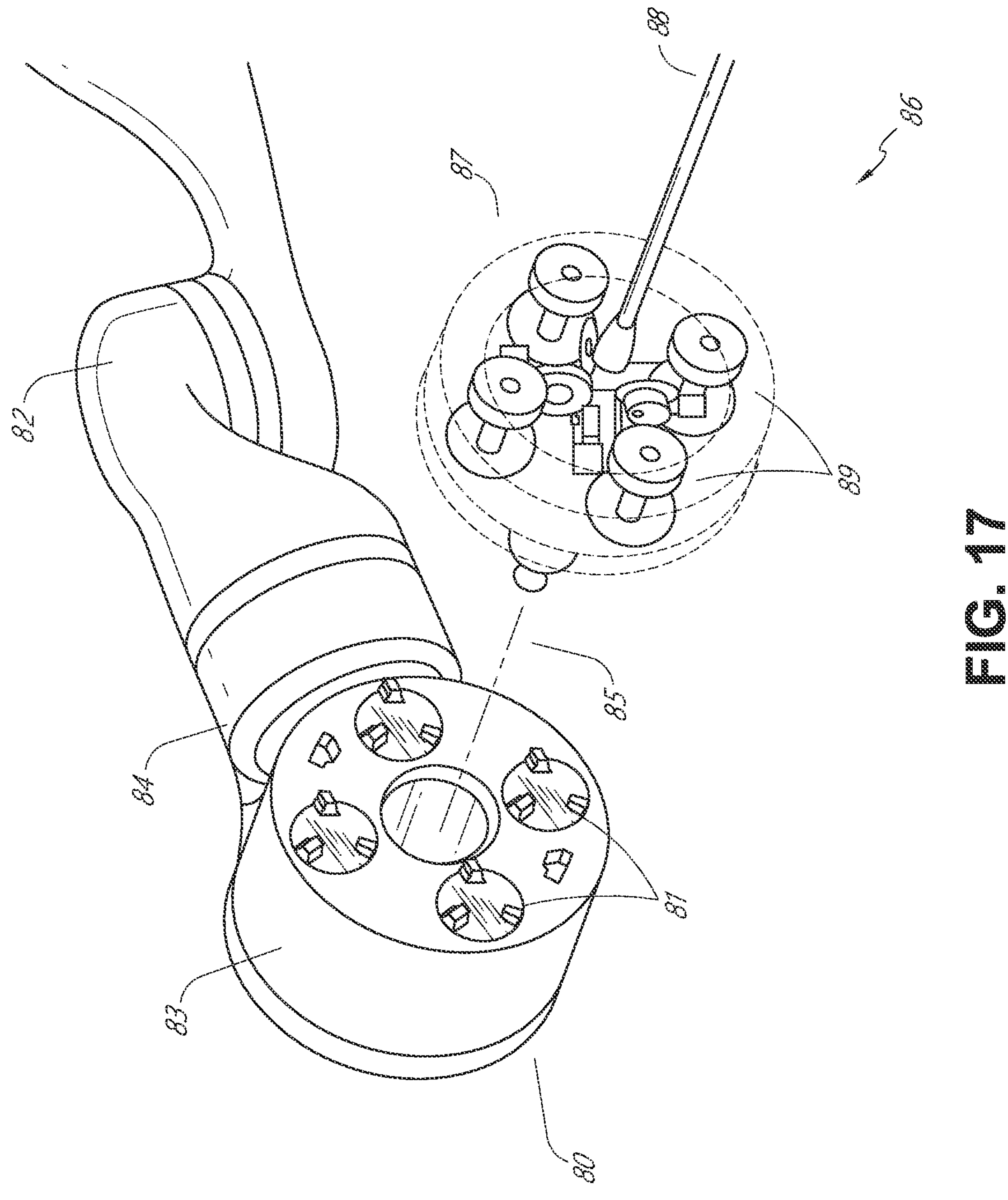
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the nonrotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
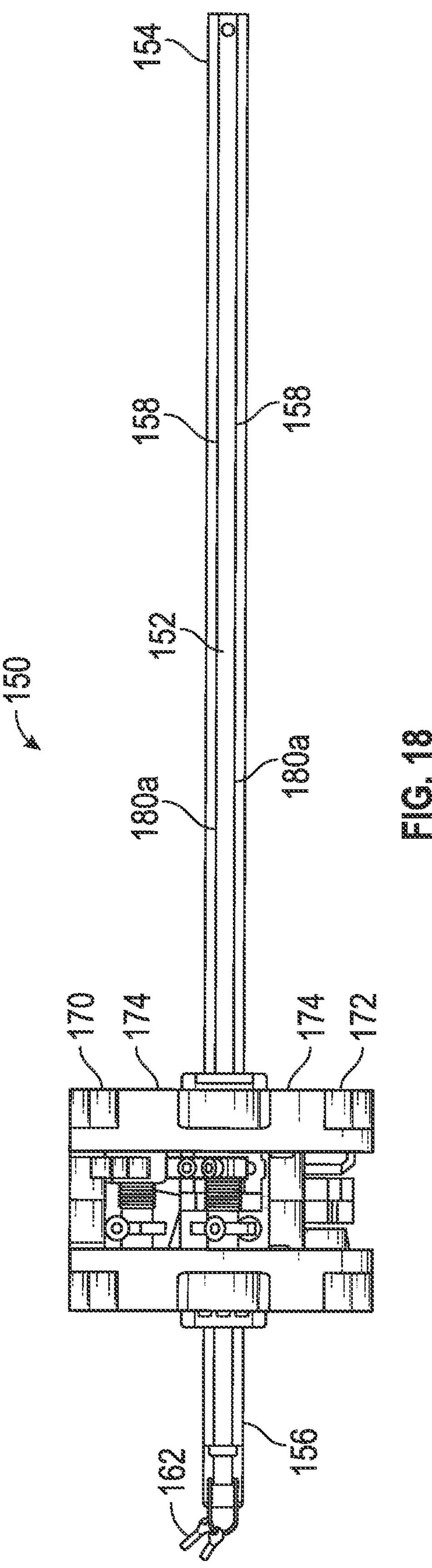
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
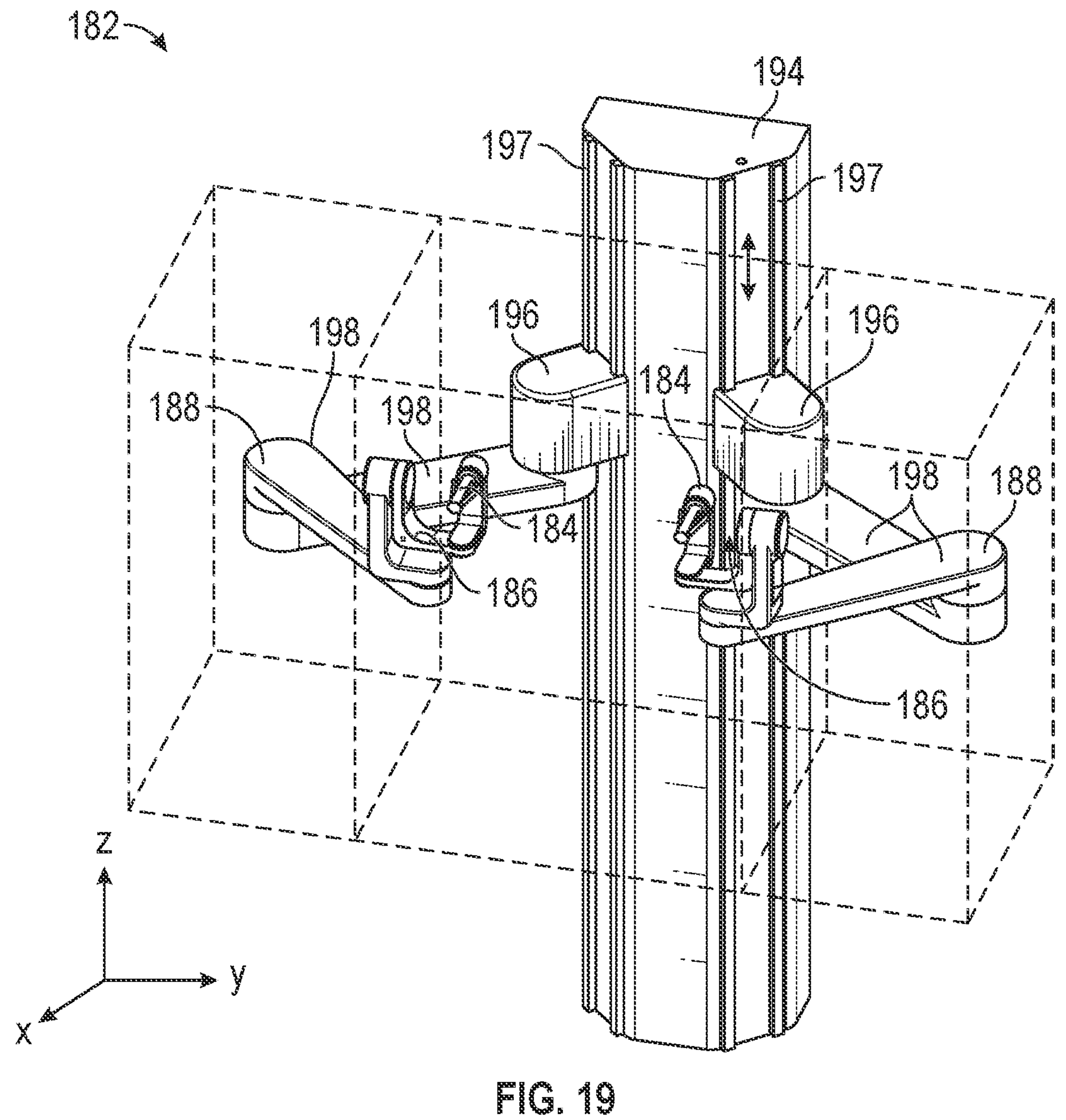
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
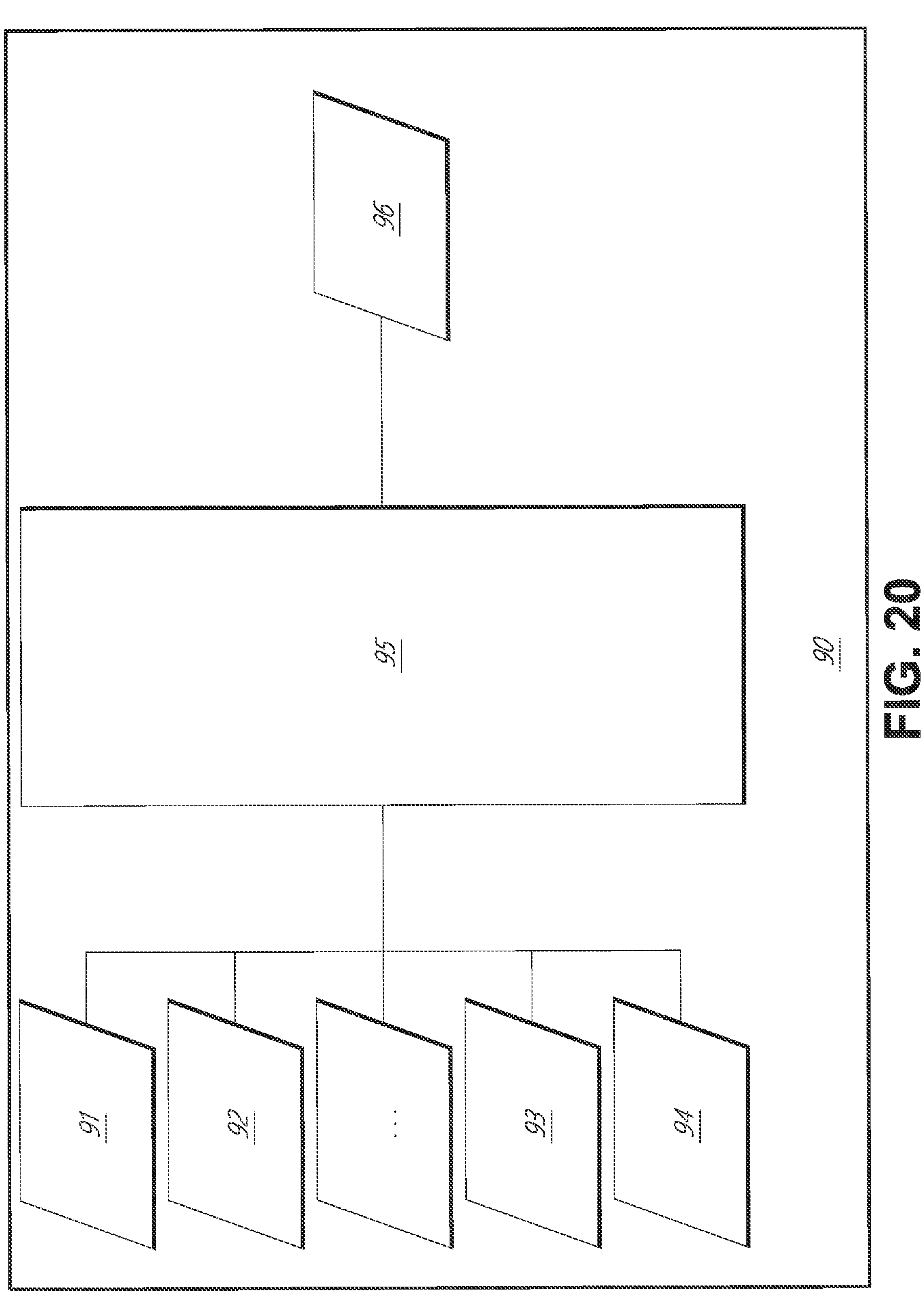
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Adjustment of External Load Thresholds

Figure 21:
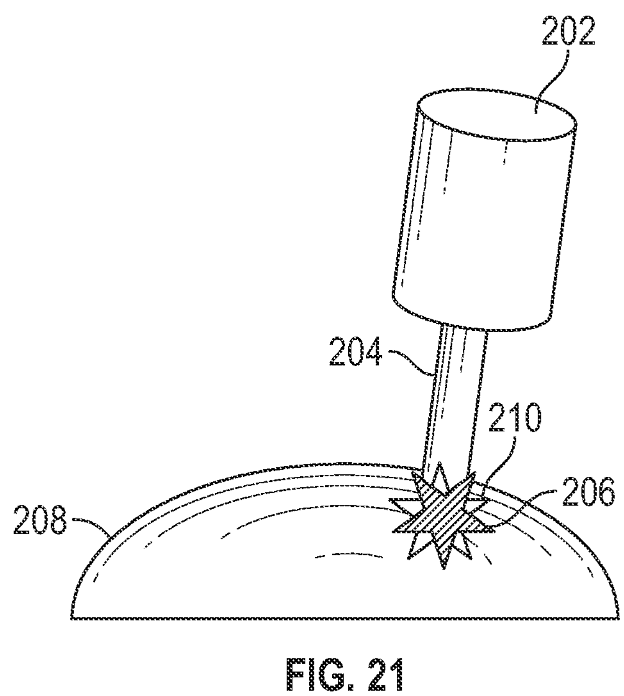
FIG. 21 illustrates an example instrument driver configured to be coupled to a cannula inserted into a patient's body wall in accordance with aspects of this disclosure.

Embodiments of the disclosure relate to systems and techniques for adjusting external load thresholds for one or more robotic arms of a robotic surgical system (e.g., the system 10 of FIG. 1 or the system 140A of FIG. 14). FIG. 21 illustrates an example instrument driver 202 configured to be coupled to a cannula 204 inserted into a patient's body wall 208 in accordance with aspects of this disclosure. As described below, the cannula 204 may be inserted into the body wall 208 at an incision 210 and can be configured to pivot about a remote center of motion 206.

The configuration illustrated in FIG. 21 may be used, for example, during a laparoscopic procedure to provide access to the patient's internal tissue. In some implementations, a robotic system can be used to control laparoscopic instrument(s) during a surgical procedure via the instrument driver 202 inserted into the patient via the cannula 204 as shown in FIG. 21.

During a surgical procedure, a robotic arm may exert large forces on the body wall 208 of a patient as the robotic arm moves through a workspace. The instrument driver 202 can be connected to the distal end of the robotic arm, thereby enabling the robotic arm to control movement of a medical instrument via the instrument driver 202. The medical instrument can be inserted through the cannula 204 into the patient. During the surgical procedure, the robotic arm can pivot the cannula 204 about an incision 210 of the patient. The incision 210 may define the location at which the cannula 204 and medical instrument intersect the body wall 208.

The point at which the cannula 204 and medical instrument can pivot may be referred to generally as the remote center of motion 206 (also referred to simply as a "remote center" or "RCM"). In certain implementations, the remote center of motion 206 may be a static point in space at which the system constrains the motion of the cannula 204 and medical instrument using mechanical and/or software constraints. By constraining motion of the medical instrument and the cannula 204, the system is able to reduce forces exerted on the body wall 208 due to movement of the medical instrument and the cannula 204, thereby preventing or reducing trauma caused to the patient (e.g., tearing, bruising, etc. of the body wall 208).

During surgery, it may be desirable for the system to detect when an amount of a load (e.g., resulting from a force or a torque) between the cannula 204 and the body wall 208 exceeds an external load threshold value. In some embodiments, the external load threshold can be based on load threshold(s) of a full robotic arm, individual joints of the robotic arm, or any combination thereof, which can advantageously vary during a procedure. For example, the external load threshold value may be set as a value used to prevent the forces or torques exerted on the body wall 208 from causing injury to the patient as a matter of safety. In certain robotic surgical systems, the system may use a single force threshold value (e.g., about 30 N) as the external load threshold, whereby the robotic surgical system can be configured to enter a fault state if the force acting on the cannula 204 exceeds the force threshold value, as detected by one or more sensors on the robotic arm. In certain implementations, the robotic system may be capable of entering each of its respective robotic arm(s) individually into a fault state, such that a given robotic arm is entered into a fault state when the given robotic arm experiences a load exceeding a corresponding external load threshold.

Each of the robotic arms can include one or more brakes configured to hold the current poses of each of the robotic arms when in such a fault state. For example, in the event that the system determines that a robotic arm has applied a force to the body wall of the patient exceeding the force threshold value (or vice versa), brakes in the robotic arm can be actuated to maintain its joint poses, thereby preventing additional movement which may injure or cause trauma to the patient. In addition, in some embodiments, the brakes may be applied in a gradual manner such that the amount of braking increases as the force applied by the robotic arm to the body wall (or vice versa) approaches the force threshold value. Note that in other embodiments, while a fault state may be triggered once a detected force exceeds a force threshold value, a robotic arm can simply stop moving without causing brakes to engage.

Although the external load threshold value may be set to prevent movement of robotic arms and/or medical instruments attached thereto in order to protect the patient, the external load threshold value may also be set such that the brakes of the robotic arms can provide sufficient braking force to maintain the current poses of the robotic arms when in a fault state and/or when the robotic arm is powered off. For example, each brake on the robotic arms may be configured to provide a predetermined braking force. The robotic system can define a set holding torque for each brake, which may be less that the predetermined braking torque or force. The amount of force required to hold a given robotic arm pose can be dependent on the current pose of the robotic arm and any external forces being applied to the robotic arm (e.g., a force between the body wall 208 and a medical instrument attached to the robotic arm). Thus, the robotic system can adjust the external load threshold such that if the robot enters into a fault state and the brakes are engaged, the brakes would be able to hold the robotic arm and its external loads such that the robotic arm would not move.

Figure 22:
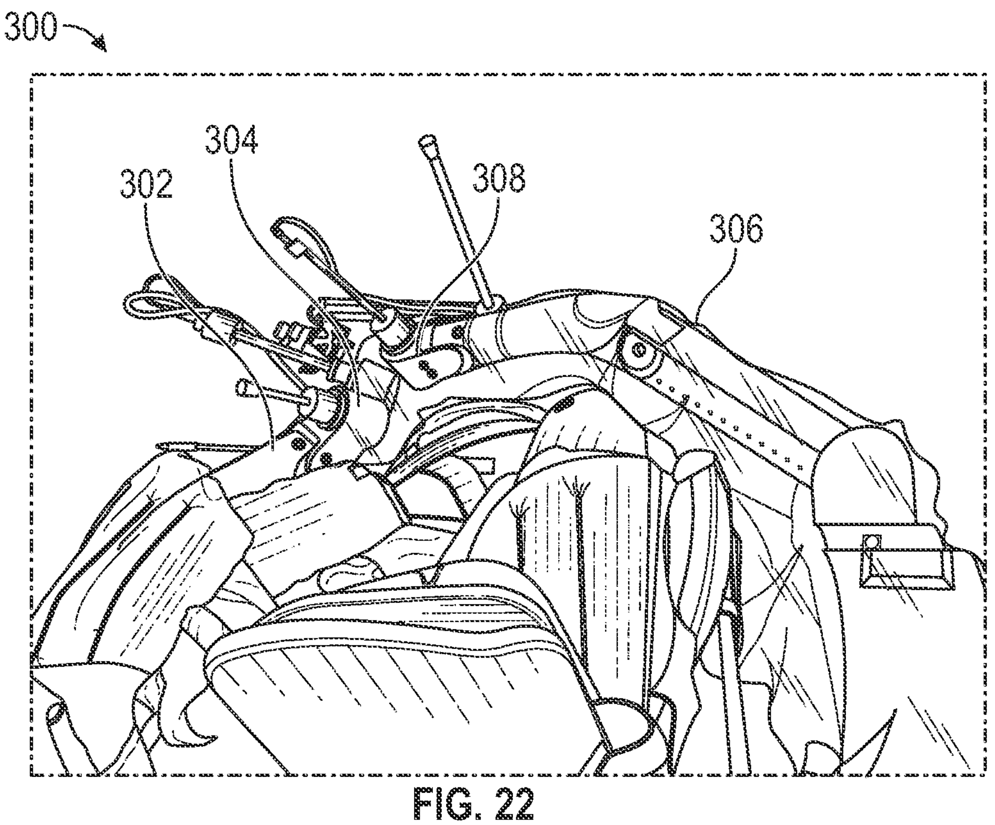
FIG. 22 illustrates an example robotic system performing an exemplary surgical procedure in accordance with aspects of this disclosure.

FIG. 22 illustrates an example robotic system 300 performing an exemplary surgical procedure in accordance with aspects of this disclosure. The robotic system 300 includes a first robotic arm 302 having a first device manipulator 304, as well as a second robotic arm 306 having a second device manipulator 308. At the stage of the procedure illustrated in FIG. 22, the second robotic arm 306 is in a more outstretched pose compared with the first robotic arm 302. Due to the pose of the second robotic arm 306, the forces applied to the second device manipulator 308 of the second robotic arm 306 may result in comparatively larger torque(s) on the joints of the second robotic arm 306 as compared to, for example, the first robotic arm 302. In contrast, the pose of the first robotic arm 302 may apply forces to the first device manipulator 304 resulting in relatively lower torques applied to the joints of the first robotic arm 302. That is, the poses of the first and second robotic arms 302, 306 can affect the amount of torque that results from the leverage of forces exerted on the first and second robotic arms 302, 306.

As described above, in certain implementations the robotic system 300 can use a single external load threshold as the maximum allowable load applied to the first and second device manipulators 304, 308 before the system enters a fault state. Since the first and second robotic arms 302, 306 can be positioned in various different poses within the operating environment, the external load threshold can be set to a value to such that the brakes of the first and second robot arms 302, 306 can prevent further motion of the robotic arms 302, 306 in the event the robotic system enters a fault state (e.g., even when the first and second robot arms 302, 306 are in outstretched poses).

In some situations, a surgeon may want to continue to drive a robotic arm beyond the single external load threshold. For example, though not shown in FIG. 21, the surgeon may command a robotic system to perform a tenting procedure that involves driving a robotic arm to position a cannula 204 to prop up a body wall 208, thereby increasing the volume of the patient's body cavity. During such a tenting procedure, a surgeon may want to continue to drive the robotic arm, without having the system enter a fault state due to forces on the cannula 204 (or the instrument driver 202) exceeding the single external load threshold. In systems which enforce a single external load threshold, a tenting procedure may result in the system entering a number of fault states, despite the desire of the surgeon to continue driving the robotic arm to provide tenting. Aspects of this disclosure therefore advantageously provide techniques for dynamically adjusting an external load threshold, enabling certain procedures which may otherwise be vulnerable to entering one or more fault states.

Figure 23A:
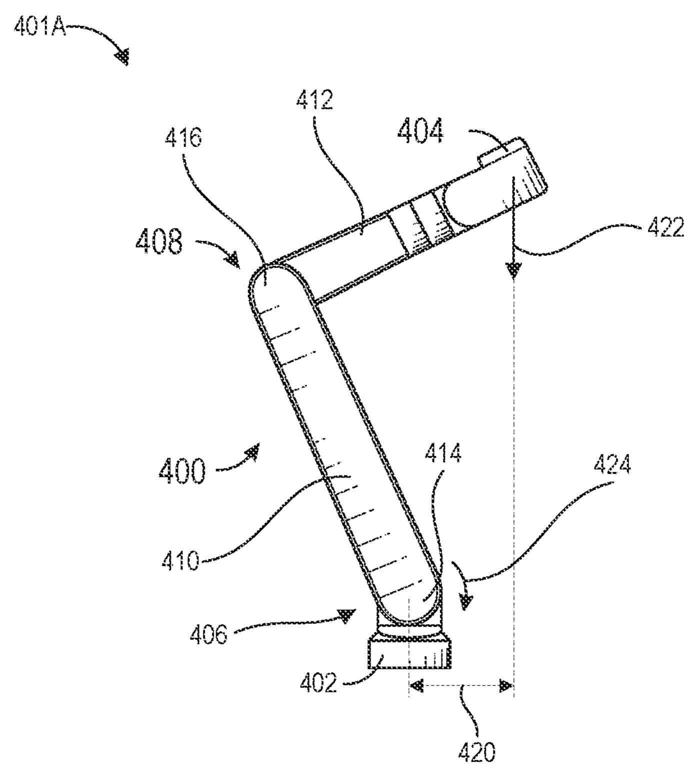
FIGS. 23A and 23B illustrate an example robotic arm that can be used as part of a robotic system for the dynamic adjustment of external load thresholds in accordance with aspects of this disclosure.
Figure 23B:
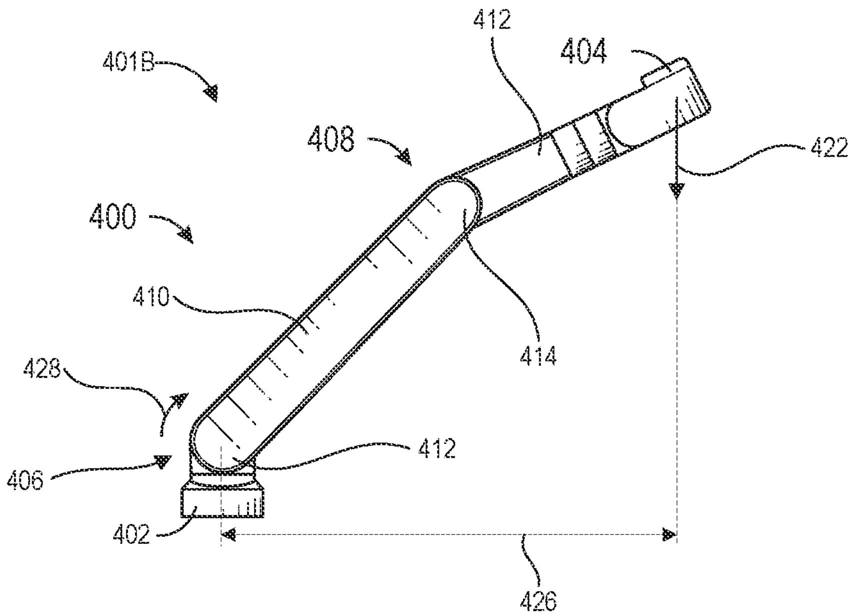

FIGS. 23A and 23B illustrate an example robotic arm 400 that can be used as part of a robotic system for the dynamic adjustment of external load thresholds in accordance with aspects of this disclosure. Specifically, FIG. 23A illustrates the robotic arm 400 in a first pose 401A and FIG. 23B illustrates the robotic arm in a second pose 401B. With reference to FIGS. 23A and 23B, the robotic arm 400 includes a base 402, an instrument driver 404, a first joint 406, a second joint 408, a first link 410, and a second link 412. The base 402, the first link 410, and the second link 412 are connected via the first joint 406 and the second joint 408. The first joint 406 includes a first brake 414, and the second joint 408 includes a second brake 416. The first and second brakes 414 and 416 may be positioned inside of the first and second joints 406 and 406, respectively.

Rather than having a single external load threshold that defines the maximum amount of load that a robotic arm 400 can apply to a body wall prior to entering a fault state, in some implementations, the robotic system can dynamically adjust the value of the external load threshold, for example, during a medical procedure or intraoperatively. Thus, the value of the load applied to body wall by the robotic arm 400 before the robotic system enters a fault state may be dependent on the current, adjustable value of the external load threshold. In some implementations, the robotic system can adjust the external load threshold based at least in part on a pose of the robotic arm 400. Advantageously, by adjusting the load thresholds, the robotic system can reduce the number of workflow stoppages (e.g., by minimizing the number of false positives or unwanted entries into the fault state), while giving a user of the robotic system control over the amount or degree force that the robotic system may apply to the patient, e.g., during a particular type of medical procedure.

The first pose 401A and the second pose 401B of the robotic arm provide exemplary scenarios in which the robotic system can benefit from the dynamic adjustment of the external load threshold. For example, in the first pose 401A, the robotic arm 400 is in a relatively more upright position compared to in the second pose 401B where the robotic arm 400 is in a relatively more extended position. In the second pose 401B, the robotic arm 400 experiences a higher gravitational load than the robotic arm 400 in the first pose 401A due to leverage. For example, in the first pose 401B, a first torque 424 may be applied at the first joint 414 due to a first downward force 422 at the instrument driver 404 acting a first distance 420 from the first joint 414. In the second pose 401B, a second torque 428 may be applied at the first joint 414 due to the first downward force 422 at the instrument driver 404 acting at a second distance 426 from the first joint 414. Due to the difference in the lengths of the first distance 420 and the second distance 426, the second torque 428 may be significantly greater than the first torque 424.

In addition to external loads applied to the robotic arm 400 (e.g., applied at the instrument driver 404 due to a medical instrument attached thereto and/or applied at other points along the robotic arm 400, for example, due to a collision), the force of gravity on the robotic arm 400 will also contribute to the torques applied at the first and second joints 406 and 406 of the robotic arm 400. The torques experienced by the first and second joints 406 and 406 due to the force of gravity may also be dependent on the pose of the robotic arm 400 in a similar fashion to the force 422 applied to the instrument driver 404 as discussed above.

In addition to the load on the robotic arm 400 due to gravity, the robotic arm 400 can also experience an inertial load based on movement of the robotic arm 400. Due to the various poses that the robotic arm 400 is capable of, the robotic arm 400 can handle a different amount of external load from contact with the patient and/or the external environment, in addition to the loads due to gravity and inertia. In other words, as the pose of the robotic arm 400 changes, the amount of external load 400 that the robotic arm 400 can safely handle (e.g., the acceptable amount of external loads) changes as well.

In aspects of this disclosure, the robotic system can determine the gravitational load and the inertial load of the robotic arm 400 based on the pose of the robotic arm 400 and determine the external load threshold based at least in part on the gravitational load and the inertial load. The robotic system may also determine the external load threshold of the robotic arm 400 based on a maximum safe load capability of the robotic arm 400. For example, the maximum safe load capability may be based on the amount of braking force that can be provided by the first brake 414 and/or the second brake 416.

In some implementations, the robotic system will use a fixed value for the maximum safe load capability. In other implementations, the robotic system may adjust the maximum safe load capability, for example, based on time or temperature. The maximum safe load capability may be dependent on environmental factors or measurements, e.g., the robotic system may adjust the maximum safe load capability based on a measured temperature of the environment or a measured temperature of the robotic arm 400 (e.g., at one or more of the joints 406, 408). In some implementations, the robotic system can determine the external load threshold based on the maximum safe load capability minus at least one of the gravity load and the inertial load.

Since the load applied to each of the joint 406, 408 may differ and is dependent on the pose of the robotic arm 400, the robotic system can set a separate external load threshold for each of the joints 406, 408 of the robotic arm 400. In setting the external load thresholds, the system can determine a load applied to each of the joints 406, 408 due to at least one of gravity or inertia of the robotic arm 400 and set the external load thresholds for each of the joints 406, 408 based on a maximum safe load capability of the corresponding joint 406, 408 and the at least one of the gravity load and the inertial load. In addition, each of the joints 406, 408 may have a different capability (e.g., maximum torque) for holding a current pose, and each of the joints 406, 408 may be oriented in different directions, depending on the pose of the robotic arm 400. By combining the individual capabilities of each of the joints 406, 408 making up the robotic arm 400, the system can determine a maximum safe load capability for the robotic arm 400. In some implementations, in combining the individual joint 406, 408 capabilities, the system may take into account the directions of each of the joint 406, 408 capabilities (e.g., taking into account the current pose of the robotic arm 400).

A specific example of values which may be determined by the robotic system will be provided in connection with FIG. 22. However, the values of this example are provided merely to illustrate one example and are not limiting on the other aspects of this disclosure. In this example, a given joint of each of the first robotic arm 302 and the second robotic arm 306 can support about 100 N-m of torque, which may be considered the maximum safe load of the given joint. In this example, the weight of each of the first and second robotic arms 302 and 306 is about 100 N.

The center of mass for the second robotic arm 306 may be located about 0.5 m laterally outstretched from the base of the second robotic arm 306. Thus, the gravity and/or inertial loads (e.g., based on current motion of the second robotic arm 306) that are exerted on the joint at the base of the second robotic arm 306 can be determined as substantially equal to a torque of about 50 N-m. Since the joint can support about 100 N-m of torque, the joint can support an additional about 50 N-m of torque applied from other objects or forces in the environment, and thus the robotic system can set the external load threshold for the joint of the second robotic arm 306 to be about 50 N-m.

Continuing with the example, for the second robotic arm 302, the center of mass is about 0.2 m laterally outstretched from the base of the first robotic arm 302, such that the gravity and/or inertial loads that are exerted on a joint of the first robotic arm 302 can be determined as substantially equal to a torque of about 20 N-m. Accordingly, the joint of the first robotic arm 302 can now support an additional 80 N-m of torque applied from other things in the environment, and thus, the robotic system can set the external load threshold for the joint of the first robotic arm 302 to be about 80 N-m.

In this example, the robotic system is able to dynamically adjust the external load thresholds for joint(s) of each of the robotic arms depending on their current pose and position, such that the external load thresholds are different for each of the robotic arms. The external load thresholds can therefore be adjusted dynamically by the robotic system, and may even be adjusted when the first and second robotic arms 302, 306 are in motion by taking into account the inertial loads of the first and second robotic arms 302, 306.

In some implementations, the robotic system can be configured to measure the loads applied to the robotic arm(s) 302, 306, 400 (e.g., the loads from the cannula and from other external objects). The robotic system can compute the amount of torque that the brakes 414, 416 would be required to support or counterbalance in the event that the robotic system enters a fault state. In response to determining that the required amount of braking power or brake torque is approaching or within a threshold value of the capability limits of the brakes 414, 416, the robotic system can prevent further movement of the robotic arm(s) 302, 306, 400 to avoid a potentially unsafe situation (e.g., a pose of one or more robotic arms that cannot be maintained using the brakes 414, 416).

There may be a number of different techniques that can be used by the robotic system to determine the loads on a given robotic arm 400 or portion(s) thereof. In some implementations, the robotic arm 400 can include one or more sensors configured to detect external load(s). For example, the one or more sensors may be configured to generate signals indicative of the loads on the robotic arm 400. Examples of sensors for determining loads on a joint can include: one or more torque sensors, which may be located at the joints 406, 408; a load cell at the end effector 404; and load cells positioned between the joints 406, 408, among other embodiments. In some embodiments, sensors can be used that detect current measurements from motors in the joints 406, 408.

Figure 24A:
FIGS. 24A and 24B illustrate an example implementation of a load cell in accordance with aspects of this disclosure.
Figure 24A:
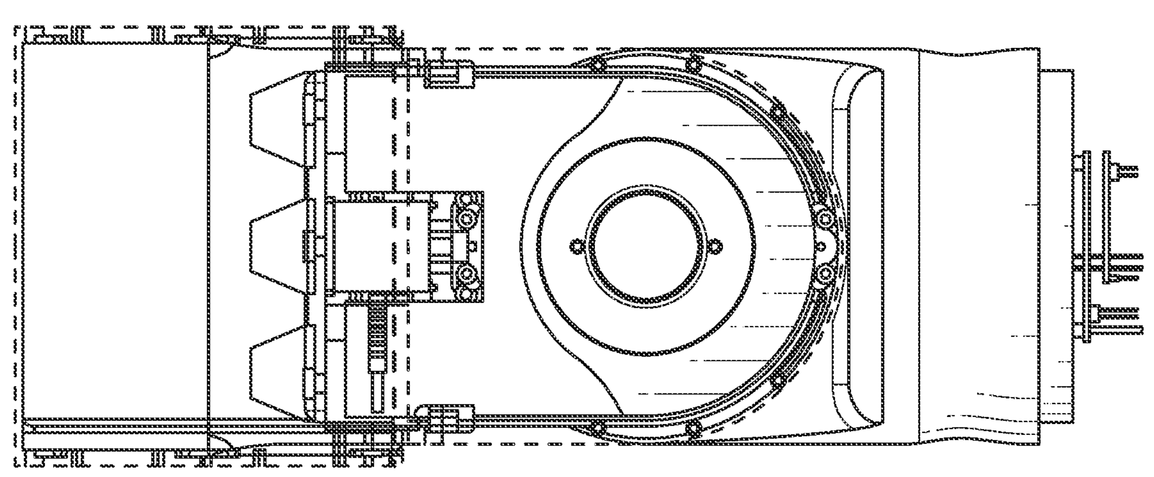
Figure 24B:
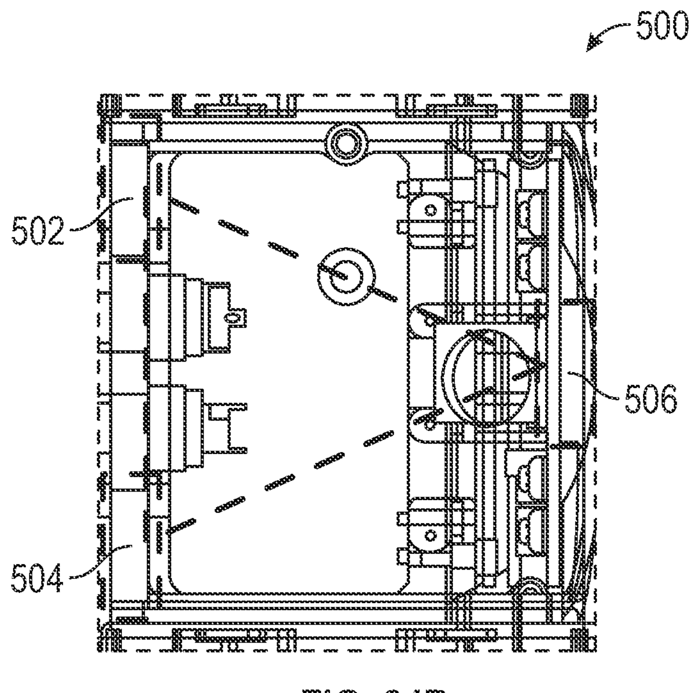

FIGS. 24A and 24B illustrate an example implementation of a load cell system or assembly 500 in accordance with aspects of this disclosure. The load cell system 500 may include a first load cell 502, a second load cell 504, and a third load cell 506 in a particular arrangement (e.g., a tripod arrangement as shown in FIG. 24B). Each of the load cells 502, 504, 506 can include at least one flexure and associated strain gauge. In some implementations, the load cell system 500 can sense load in multiple axes, such as, for example, in six degrees-of-freedom (DOFs). In certain implementations, each joint (e.g., the joints 406, 408 of FIGS. 23A and 23B) of a robotic arm can sense a load in one direction. In these implementations, the system can receive information regarding the loads sensed in each of the directions of each joint and combine the loads together to determine, for example, a net load and direction at the end effector of the robotic arm (and/or at another location of the robotic arm).

In some implementations, rather than sensing loads on the joints 414, 416 of a robotic arm 400, the robotic arm can sense loads directly on one or more links 410, 412 of the robotic arm 400. Examples of sensors that can be used to determine loads on a robotic arm link 410, 412 include capacitive contact sensors (e.g. force strips), load sensors, etc.

Figure 25:
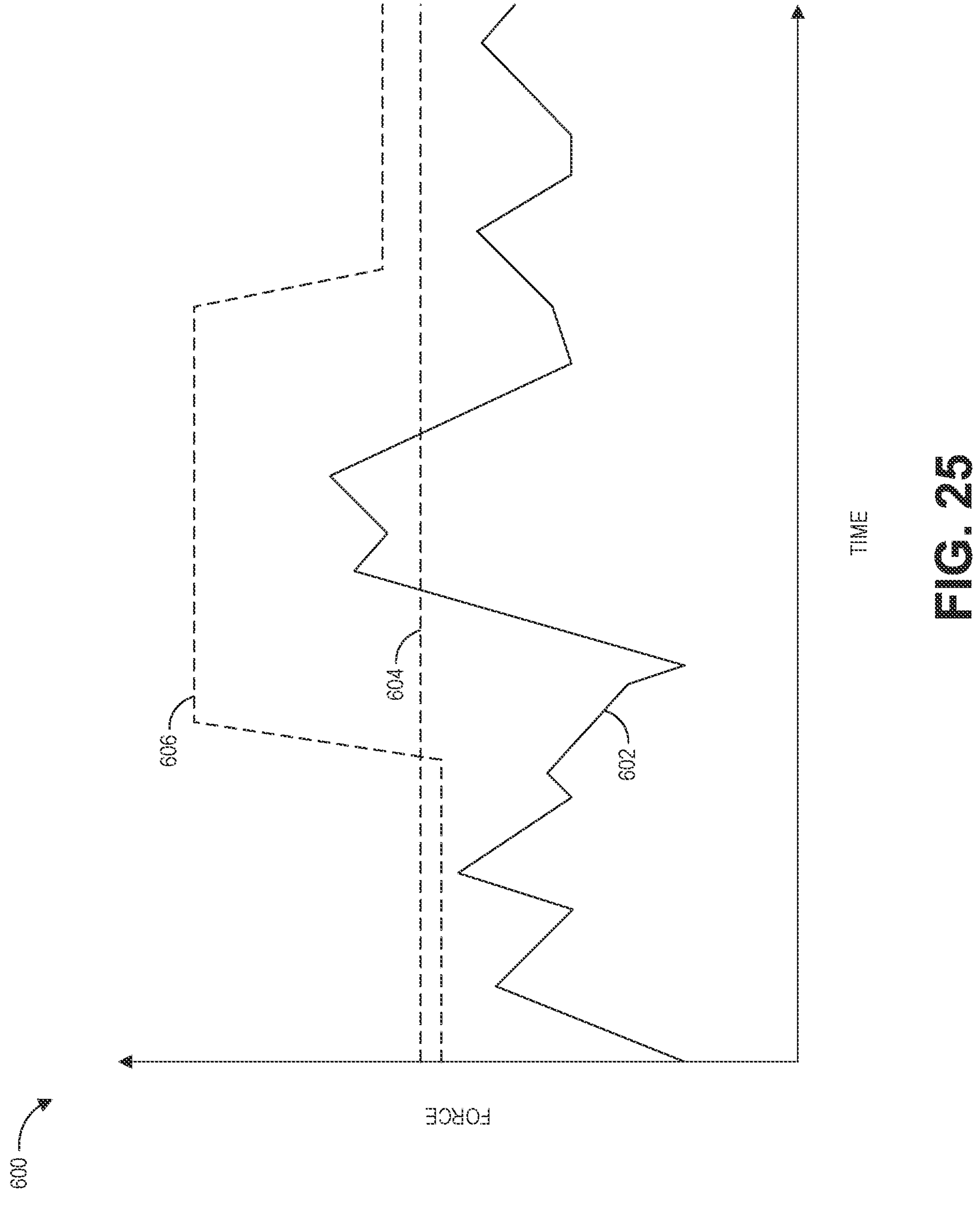
FIG. 25 is an example graph illustrating the dynamic adjustment of the external load threshold in accordance with aspects of this disclosure.

FIG. 25 is an example graph 600 illustrating the dynamic adjustment of the external load threshold in accordance with aspects of this disclosure. In particular, the graph illustrates a tracing/signal representing load applied to an instrument driver 602 (e.g., the instrument driver 404 shown in FIGS. 23A and 23B), a static external load threshold 604, and an adjustable external load threshold 606. As shown in FIG. 25, the load applied to the instrument driver 602 may exceed the static external load threshold 604 for a certain time period. Thus, the static external load threshold 604 may result in the robotic system entering a fault state in response to the load applied to the instrument driver 602 exceeding the static external load threshold 604.

In contrast, the adjustable external load threshold 606 may change over time, for example, in response to changes in pose of the robotic arm. Due to the changes in the external load threshold 606, the load applied to the instrument driver 602 does not exceed the adjustable external load threshold 606 where the load applied to the instrument driver 602 would have exceeded the static external load threshold 604. Thus, by using the adjustable external load threshold 606, the robotic system is able to avoid entering a fault state that would otherwise have occurred when using the static external load threshold 604.

In certain implementations, the robotic system can also combine the ability to dynamically adjust the external load threshold with the ability to dynamically move a remote center (e.g., via software) to minimize the amount of load on the remote center, as will be explained in further detail below. Together, these two techniques can help the robotic system to avoid workflow stoppages by dynamically adjusting the position of the remote center while increasing reach of the robotic arms.

3. Adjustment of Remote Centers

Embodiments of the disclosure also relate to systems and techniques for adjusting the position of remote center(s). As described above and illustrated in FIG. 21, a robotic arm can pivot the cannula 204 about a remote center 206 through an incision 210 of the body wall 208. It is generally desirable to maintain the location remote center 208, either mechanically or via software. However, there are some situations where it may be desirable for the robotic system to adjust the location of remote center 208 via software.

Figure 26:
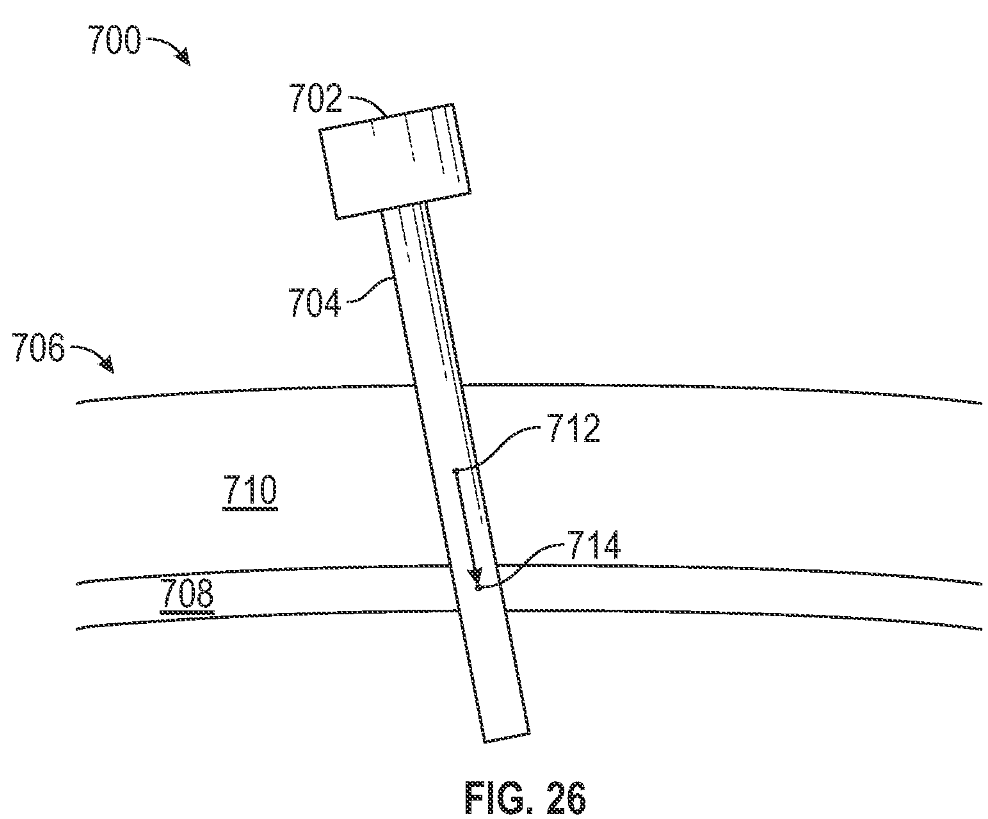
FIG. 26 illustrates one example configuration of an instrument driver and cannula having an adjustable remote center in accordance with aspects of this disclosure.

FIG. 26 illustrates one example configuration 700 of an instrument driver 702 and cannula 704 having an adjustable remote center 712, 714 in accordance with aspects of this disclosure. In the illustrated configuration 700, the instrument driver 702 is coupled to a cannula 704 inserted into a patient's body wall 706. The body wall 706 includes a muscle layer 708 and a fat layer 710. A robotic arm is configured to control the instrument driver 702 to pivot the cannula 704 about a remote center of motion 712, 714, The initial location of the remote center 712 may be located a predetermined distance from the instrument driver 702. For example, the predetermined distance may be set based on characteristics of the body wall 706 for the average patient. However, for certain patients, such as overweight and/or obese patients, the fat layer 710 of the body wall 706 may be thicker than the fat layer 710 of an average patient. Additionally, the fat layer 710 may be more easily deformed based on movement of the cannula 704 than the muscle layer 708, and the muscle layer 708 may be more likely to be injured when forces from the cannula 704 are applied to it. Thus, if the remote center 712 is located in the fat layer 710, when the cannula 704 is pivoted around the remote center 712, such pivoting may result in forces applied to the muscle layer 708. In order to reduce the forces applied to the muscle layer 708, the robotic system can adjust the position of the remote center from a first position 712 within the fat layer 710 to a second position 714 within the muscle layer 708. In some implementations, the robotic system can adjust the position of the remote center from a first position 712 intraoperatively.

In some implementations, the robotic system is configured to detect that the cannula 704 is exerting an excessive force on an anatomy of the patient and adjust the position of the remote center 712, 714 based on the detected excessive force. For example, the robotic system can measure a force exerted on the cannula 704 by the body wall 706 and determine whether the measured force is greater than a threshold force. In response to determining that the measured force is greater than the threshold force, the robotic system can adjust the position of the remote center of motion 712, 714 based on the measured force between the cannula 704 and the body wall 706 of the patient. In some implementations, the robotic system may move the position of the remote center of motion 712, 714 in a direction that reduces the measured force. For example, the robotic system may determine the direction of the force exerted on the cannula 704 and move the remote center of motion 712, 714 in a direction that has a component in the opposite direction of the force exerted on the cannula 704. Although FIG. 26 illustrates moving the remote center of motion 712, 714 in a direction along the longitudinal axis of the cannula 704, the robotic system can be configured to move the remote center of motion 712, 714 in any direction.

In some implementations, the robotic system may constrain the movement of the remote center of motion 712, 714 within a threshold distance of the initial location of the remote center of motion 712, 714. The robotic system can also allow the user to selectively allow or disallow the automated movement of the remote center of motion 712, 714 to reduce the force exerted on the cannula 704. The adjustment of the position of the remote center of motion 712, 714 by the robotic system may be desirable to reduce loading on the body wall 706 of the patient and thereby prevent or reduce injury. One example situation in which it can be beneficial to adjust the position of the remote center of motion 712, 714 is when a patient's position shifts on a table (e.g., the supporting platform 38 of FIGS. 5 and 9), thereby causing forces to be applied to the cannula 704. By detecting the forces applied to the cannula 704 in this situation, the robotic system can trigger movement of the position of the remote center of motion 712, 714 in response to movement of the patient on the patient platform. In some implementations, the system may alert a user to the forces applied to the cannula 704 which may be responsive to movement of the patient and receive an input from the user to adjust the position of the remote center of motion 712, 714.

Figure 27:
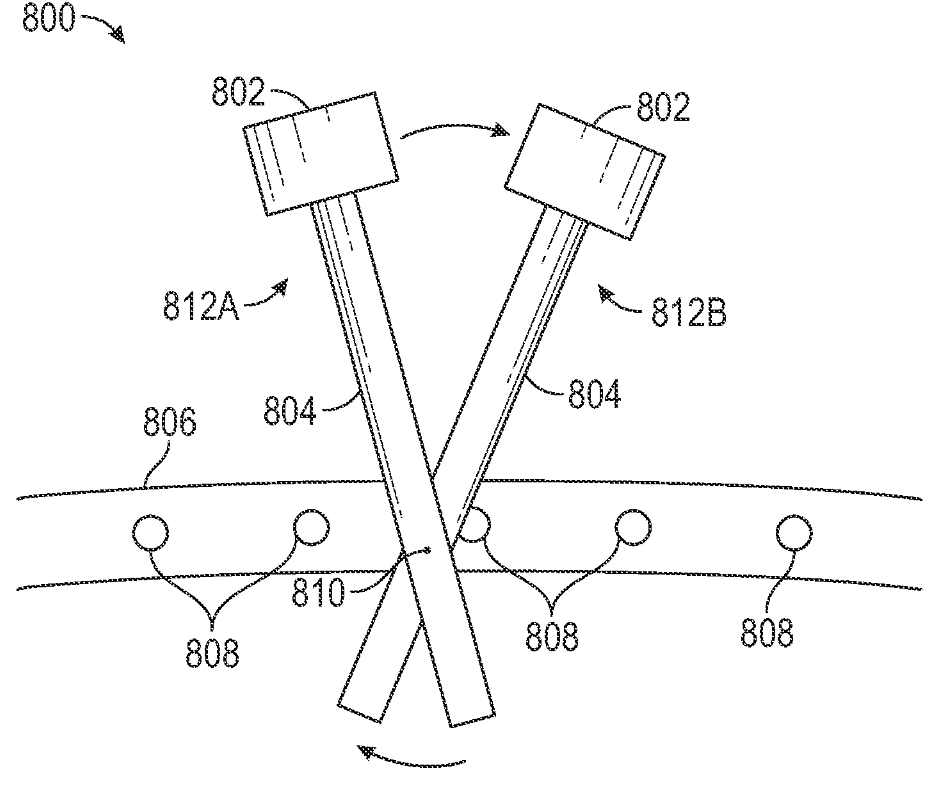
FIG. 27 illustrates another example configuration of an instrument driver and cannula having an adjustable remote center in accordance with aspects of this disclosure.

FIG. 27 illustrates another example configuration 800 of an instrument driver 802 and cannula 804 having an adjustable remote center 810 in accordance with aspects of this disclosure. In the configuration 800 of FIG. 27, the cannula 804 may be inserted through a patient's body wall 806 in between the patient's ribs 808.

During a medical procedure, the instrument driver 802 can pivot the cannula 804 in order to gain access to a different location. For example, the instrument driver 802 can pivot the cannula 804 with respect to the remote center of motion 810 from a first pose 812A to a second pose 812B. In the first pose 812A, the cannula 804 may experience forces within an expected range due to the surgical procedure. However, as the cannula 804 is pivoted into the second pose 812B, the cannula 804 may hit one of the ribs 808, leading to a large unexpected force. The robotic system can be configured to measure the force due to the cannula 804 hitting the rib 808 and adjust the position of the remote center of motion 810 based on the measure force. In some implementations, the robotic system, in response to detecting the force on the cannula 804 has increased or is increasing, may adjust the position of the remote center of motion 810 to reduce the measured/detected force on the cannula 804 before the force reaches a force threshold value. By adjusting the position of the remote center of motion 810 prior to reaching the force threshold value, the robotic system can avoid entering into the fault state and disrupting the surgical workflow. For example, if the cannula 804 is pivoted towards the second pose 812B, the system may move the remote center of motion 810 toward the left side of the figure to avoid a collision between the cannula 804 and the rib 808.

In some implementations, the robotic system can enter a fault state to restrict or prevent further movement of the robotic arm in response the force exerted on the cannula 804 reaching the force threshold in order to prevent possible injury to the patient. For example, restricting further movement may involve the robotic system restricting the allowable directions of motion of the robotic arm to directions that will reduce the external load, thereby allowing the user to avoid or move away from a potential excess external load on the robotic arm.

In certain implementations, the robotic system may also be configured to adjust the position of the remote center of motion 810 automatically to enhance the reach and effective workspace of a robotic arm. For example, the robotic system can automatically move the remote center of motion 810 to enhance the reach and/or the effective workspace of the robotic arm. In certain implementations, the robotic system can also enable the user to allow or disallow the automatic movement of the remote center of motion 810 to enhance the reach of a robotic arm. For example, the robotic system may have a global, user-defined parameter that can either allow or disallow automatic movement of the position of the remote center of motion 810 and/or one or more user-defined parameters that can either allow or disallow automatic movement of the position of the remote center of motion 810 to achieve certain goals (e.g., a parameter for automated reduction of the force at the cannula 804, parameter for automated enhancing of the reach of a robotic arm, or parameter(s) to achieve other goals via automated remote center 810 movement).

In one example, the operator can weigh the expected harm of moving the remote center of motion 810 against the benefits of increased access to an operative site and select whether to allow automatic movement of the remote center of motion 810 accordingly. In this situation, the remote center of motion 810 can be constrained to move within a predetermined area (e.g., within a sphere or square of a defined size). The movement of the remote center of motion 810 can also be used to provide an additional one or more DOFs of null space movement. Null space movement can refer to movement of at least a portion of a robotic arm without affecting the position of an end effector controlled by the robotic arm. Robotic arm null space movement can be used to facilitate or allow the robotic system to perform certain advantages actions, such as collision avoidance, increasing robotic arm reach, etc. The movement of the remote center of motion 810 can provide up to three additional null space DOFs in some implementations, thereby widening and adding dimensions to a null space of a robotic arm that may or may not have other null space DOFs. In some implementations, the use of remote center 810 movement to provide null space DOFs may be a user selectable option. In addition, the robotic system can limit the amount of remote center 810 movement to within a predetermined distance (in 1, 2, or 3 dimensions) of the point where the remote center was initial set by the user.

In certain implementations, the robotic system can also be configured to adjust the position of the remote center of motion 810 based on a kinematic constraint. For example, the kinematic constraint may be a collision detected by the robotic system. Thus, in response to detecting a collision (e.g., between the robotic arm and another object, such as another robotic arm, the patient, the patient platform, etc.), the robotic system can adjust the position of the remote center of motion 810 to move away from the collision. This movement of the position of the remote center of motion 810 can be a null space movement in some implementations, such that the pose of the end effector controlled by the robotic arm is unaffected. The robotic system can further be configured to avoid a collision by movement of the position of the remote center of motion 810, for example, by determining that the current commanded movement of a robotic arm will result in a collision.

Figure 28:
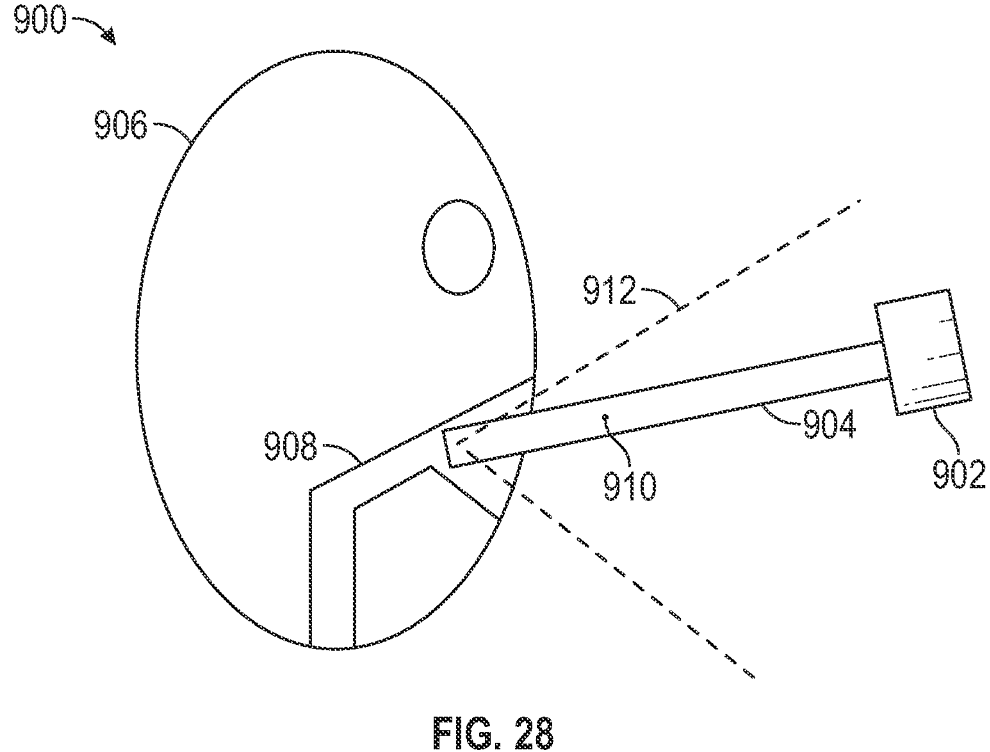
FIG. 28 illustrates yet another example configuration of an instrument driver and patient introducer having an adjustable remote center in accordance with aspects of this disclosure.

FIG. 28 illustrates yet another example configuration 900 of an instrument driver 902 and patient introducer 904 having an adjustable remote center 910 in accordance with aspects of this disclosure. In the embedment of FIG. 28, the instrument driver 902 is configured to manipulate a medical instrument (not illustrated) through the patient introducer 904 to gain access to a patient's 906 anatomy via a natural orifice 908 (e.g., the patient's mouth or throat). Although FIG. 28 illustrates an embodiment in which medical instrument can be used in a transoral procedure, aspects of this configuration 900 can also be used to perform other types of procedures which gain access through different natural orifices 908, including transoral and transvaginal procedures, among others.

As shown in FIG. 28, the instrument driver 902 may limit the movement of the patient introducer 904 to pivot about a remote center of movement 910, even though the patient introducer 904 does not penetrate the patient's 906 body wall. Since the medical instrument and patient introducer 904 do not penetrate the patient's 906 body wall, there are fewer limitations on the position of the remote center of movement 910, since adjusting the position of the remote center 910 will not exert forces on the patient's 906 body wall. Thus, the robotic system can move the remote center 910 more freely without causing trauma to the patient 906. In some implementations, the robotic system can be configured to adjust the position of the remote center 910 within a predetermined area 912. In some implementations, the predetermined area 912 may form a geometric shape, for example, a cone, a sphere, a cube, etc. By providing a relatively large predetermined area 912 in which the position of the remote center 910 can be move, the reach of the robotic arm can be improved and collisions (e.g., both of tools in the body, and of robotic arms or other components outside the body) can be avoided using the movement of the remote center 910 to provide additional null space DOFs as discussed above. Since multi-arm natural orifice configured may involve placing the robotic arms within a relatively small region as the robotic arms can gain access via the same natural orifice 908, it can be advantageous to provide these extra null space DOFs for these procedures.

4. Implementing Systems and Terminology

Implementations disclosed herein provide systems, methods and apparatus for adjusting external load thresholds and remote centers of motion for robotic systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The external load threshold adjustment and remote center adjustment functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method performed by a processor of a robotic system comprising a robotic arm, wherein the method comprises:

determining an external load threshold for a joint of the robotic arm in the robotic system based on a maximum safe load capability of the robotic arm, and adjusting the external load threshold during a medical procedure, wherein the external load threshold is adjusted in response to a change in a pose of the robotic arm.

2. The method of claim 1, further comprising determining a load applied to the joint based on at least one of a gravity load or an inertia load of the robotic arm.

3. The method of claim 2, wherein the external load threshold is further determined based on a difference between the maximum safe load capability and the at least one of the gravity load or the inertia load of the robotic arm.

4. The method of claim 1, further comprising determining a second external load threshold for a second robotic arm in the robotic system, wherein the external load threshold is different from the second external load threshold.

5. The method of claim 1, wherein the maximum safe load capability is fixed.

6. The method of claim 1, wherein the maximum safe load capability varies based on at least one of time or temperature.

7. The method of claim 1, further comprising:

determining that an external load applied to the joint exceeds the external load threshold based on a signal received from one or more sensors positioned on the robotic arm, and restricting further movement of the robotic arm in response to receiving the signal from the one or more sensors indicating that the external load applied to the joint exceeds the external load threshold.

8. The method of claim 1, further comprising maintaining, by one or more brakes of the robotic arm, a pose of the robotic arm, wherein the one or more brakes comprise a holding torque, and wherein the external load threshold is further determined based on the holding torque of the one or more brakes.

9. The method of claim 1, wherein the joint of the robotic arm includes a first joint, wherein the robotic arm includes a second joint, wherein the external load threshold includes a first external load threshold, wherein the method further comprises determining a second external load threshold for the second joint of the robotic arm in the robotic system based on a maximum safe load capability of the robotic arm.

10. A robotic system, comprising:

a robotic arm having at least one joint and an end effector;

one or more processors; and at least one computer-readable memory in communication with the one or more processors and storing computer-executable instructions to cause the one or more processors to:

determine an external load applied to the at least one joint of the robotic arm;

determine an external load threshold for the at least one joint based on a maximum safe load capability of the robotic arm and the external load applied to the at least one joint of the robotic arm; and adjust a remote center of the end effector based on a relationship of the external load to the external load threshold during a medical procedure.

11. The robotic system of claim 10, wherein the computer-executable instructions further cause the one or more processors to:

determine that the external load applied to the at least one joint exceeds the external load threshold based on a signal received from one or more sensors positioned on the robotic arm, and restricting further movement of the robotic arm in response to receiving the signal from the one or more sensors indicating that the external load applied to the at least one joint exceeds the external load threshold.

12. The robotic system of claim 10, wherein the robotic arm comprises one or more brakes configured to maintain a pose of the robotic arm based on a holding torque of the one or more brakes, and wherein the external load threshold is based on the holding torque of the one or more brakes.

13. The robotic system of claim 12, wherein the one or more brakes are further configured to maintain the pose of the robotic arm when the robotic arm is powered off or the robotic arm is in a fault state.

14. The robotic system of claim 10, wherein the at least one joint includes a first joint and a second joint, wherein the external load threshold includes a first external load threshold relating to the first joint and a second external load threshold relating to the second joint, wherein the stored computer-executable instructions are configured to cause the one or more processors to adjust the first external load threshold of the first joint and to adjust the second external load threshold of the second joint.

15. A method performed by a processor of a robotic system comprising a robotic arm, wherein the method comprises:

determining a load applied to each of a plurality of joints of the robotic arm based on at least one of a gravity load or inertia load of the robotic arm, and setting a respective maximum external load threshold for each joint of the plurality of joints based on a maximum safe load capability of the respective joint and the at least one of the gravity load or the inertia load, such that a first joint of the plurality of joints has a first maximum external load threshold while a second joint of the plurality of joints has a second maximum external load threshold, the second maximum external load threshold being different from the first maximum external load threshold.

16. The method of claim 15, further comprising adjusting the maximum external load threshold for one or more of the joints during a medical procedure.

17. The method of claim 15, wherein the maximum external load threshold is adjusted in response to a change in a pose of the robotic arm.

18. The method of claim 15, further comprising determining a second maximum external load threshold for a second robotic arm of the robotic system, wherein the maximum external load threshold is different from the second maximum external load threshold.

19. The method of claim 15, wherein the maximum safe load capability for at least one of the joints is fixed.

20. The method of claim 15, wherein the maximum safe load capability varies based on at least one of time or temperature.

* * * * *